(12) United States Patent
Couture et al.

(10) Patent No.: US 7,931,649 B2
(45) Date of Patent: Apr. 26, 2011

(54) VESSEL SEALING INSTRUMENT WITH ELECTRICAL CUTTING MECHANISM

(75) Inventors: Gary M. Couture, Longmont, CO (US); Craig Weinberg, Denver, CO (US); Philip M. Tetzlaff, Lafayette, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 1107 days.

(21) Appl. No.: 11/706,029

(22) Filed: Feb. 14, 2007

(65) Prior Publication Data

US 2008/0195093 A1 Aug. 14, 2008

Related U.S. Application Data

(63) Continuation-in-part of application No. 11/418,876, filed on May 5, 2006, now Pat. No. 7,270,664, which is a continuation-in-part of application No. 10/932,612, filed on Sep. 2, 2004, now Pat. No. 7,276,068, which is a continuation-in-part of application No. PCT/US03/28539, filed on Sep. 11, 2003.

(60) Provisional application No. 60/416,064, filed on Oct. 4, 2002.

(51) Int. Cl.
*A61B 18/14* (2006.01)
(52) U.S. Cl. ............................................. 606/51; 606/45
(58) Field of Classification Search ............... 606/45–52
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 1,822,330 A | 9/1931 | Ainslie | |
| 1,852,542 A | 4/1932 | Sovatkin | |
| 2,002,594 A | 5/1935 | Wappler et al. | |
| 2,011,169 A | 8/1935 | Wappler | |
| 2,031,682 A | 2/1936 | Wappler et al. | |
| 2,054,149 A | 9/1936 | Wappler | |
| 2,176,479 A | 10/1939 | Willis | |
| 2,305,156 A | 4/1941 | Grubel | |

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner* — Michael Peffley

(57) ABSTRACT

An end effector assembly for use with an instrument for sealing vessels and cutting vessels includes a pair of opposing first and second jaw members which are movable relative to one another from a first spaced apart position to a second position for grasping tissue therebetween. Each jaw member includes an electrically conductive tissue contacting surface connected to an electrosurgical energy source. At least one of the jaw members includes an electrically conductive cutting element disposed within an insulator defined in the jaw member. At least one channel is included in the insulator which is configured to deliver fluid between the jaw members.

8 Claims, 20 Drawing Sheets

U.S. PATENT DOCUMENTS

| | | | |
|---|---|---|---|
| 2,279,753 A | 4/1942 | Knopp | |
| 2,327,353 A | 8/1943 | Karle | |
| 2,632,661 A | 8/1948 | Cristofv | |
| 2,668,538 A | 2/1954 | Baker | |
| 2,796,065 A | 6/1957 | Kapp | |
| 3,073,311 A | 1/1963 | Tibbs et al. | |
| 3,372,288 A | 3/1968 | Wigington | |
| 3,459,187 A | 8/1969 | Pallotta | |
| 3,643,663 A | 2/1972 | Sutter | |
| 3,648,001 A | 3/1972 | Anderson et al. | |
| 3,651,811 A | 3/1972 | Hildebrandt et al. | |
| 3,678,229 A | 7/1972 | Osika | |
| 3,720,896 A | 3/1973 | Beierlein | |
| 3,763,726 A | 10/1973 | Hildebrand | |
| 3,779,918 A | 12/1973 | Ikeda et al. | |
| 3,801,766 A | 4/1974 | Morrison, Jr. | |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,016,881 A | 4/1977 | Rioux et al. | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,076,028 A | 2/1978 | Simmons | |
| 4,080,820 A | 3/1978 | Allen | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,187,420 A | 2/1980 | Piber | |
| 4,233,734 A | 11/1980 | Bies | |
| 4,236,470 A | 12/1980 | Stenson | |
| 4,300,564 A | 11/1981 | Furihata | |
| 4,311,145 A | 1/1982 | Esty et al. | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,443,935 A | 4/1984 | Zamba et al. | |
| 4,452,246 A | 6/1984 | Bader et al. | |
| 4,470,786 A | 9/1984 | Sano et al. | |
| 4,492,231 A | 1/1985 | Auth | |
| 4,493,320 A | 1/1985 | Treat | |
| 4,503,855 A | 3/1985 | Maslanka | |
| 4,506,669 A | 3/1985 | Blake, III | |
| 4,509,518 A | 4/1985 | McGarry et al. | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,624,254 A | 11/1986 | McGarry et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| 4,733,662 A | 3/1988 | DeSatnick et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,829,313 A | 5/1989 | Taggart | |
| 4,846,171 A | 7/1989 | Kauphusman et al. | |
| 4,887,612 A | 12/1989 | Esser et al. | |
| 4,938,761 A | 7/1990 | Ensslin | |
| 4,947,009 A | 8/1990 | Osika et al. | |
| 4,985,030 A | 1/1991 | Melzer et al. | |
| 5,007,908 A | 4/1991 | Rydell | |
| 5,026,370 A | 6/1991 | Lottick | |
| 5,026,371 A | 6/1991 | Rydell et al. | |
| 5,035,695 A | 7/1991 | Weber, Jr. et al. | |
| 5,037,433 A | 8/1991 | Wilk et al. | |
| 5,042,707 A | 8/1991 | Taheri | |
| 5,047,046 A | 9/1991 | Bodoia | |
| 5,078,716 A | 1/1992 | Doll | |
| 5,084,057 A | 1/1992 | Green et al. | |
| 5,085,659 A | 2/1992 | Rydell | |
| 5,099,840 A | 3/1992 | Goble et al. | |
| 5,100,430 A | 3/1992 | Avellanet et al. | |
| 5,108,392 A | 4/1992 | Spingler | |
| 5,112,343 A | 5/1992 | Thornton | |
| 5,116,332 A | 5/1992 | Lottick | |
| 5,147,357 A | 9/1992 | Rose et al. | |
| 5,151,102 A | 9/1992 | Xamiyama et al. | |
| 5,151,978 A | 9/1992 | Bronikowski et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,209,747 A | 5/1993 | Knoepfler | |
| 5,211,655 A | 5/1993 | Hasson | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,282,800 A | 2/1994 | Foshee et al. | |
| 5,282,826 A | 2/1994 | Quadri | |
| 5,290,286 A | 3/1994 | Parins | |
| 5,300,082 A | 4/1994 | Sharpe et al. | |
| 5,304,203 A | 4/1994 | El-Mallawany et al. | |
| 5,308,353 A | 5/1994 | Beurrier | |
| 5,308,357 A | 5/1994 | Lichtman | |
| 5,313,027 A | 5/1994 | Inoue et al. | |
| 5,314,445 A | 5/1994 | Degwitz et al. | |
| 5,318,589 A | 6/1994 | Lichtman | |
| 5,324,289 A | 6/1994 | Eggers | |
| D348,930 S | 7/1994 | Olson | |
| 5,326,806 A | 7/1994 | Yokoshima et al. | |
| 5,330,471 A | 7/1994 | Eggers | |
| 5,330,502 A | 7/1994 | Hassler et al. | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,350,391 A | 9/1994 | Iacovelli | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,374,277 A | 12/1994 | Hassler | |
| 5,376,089 A | 12/1994 | Smith | |
| 5,383,875 A | 1/1995 | Bays et al. | |
| 5,383,897 A | 1/1995 | Wholey | |
| 5,389,098 A | 2/1995 | Tsuruta et al. | |
| 5,389,103 A | 2/1995 | Melzer et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |

| Patent No. | Date | Inventor |
|---|---|---|
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamsom, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A * | 9/1998 | Yates et al. .......... 606/50 |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |

| | | | | | | |
|---|---|---|---|---|---|---|
| 5,817,119 | A | 10/1998 | Klieman et al. | 6,086,586 | A | 7/2000 | Hooven |
| 5,820,630 | A | 10/1998 | Lind | 6,086,601 | A | 7/2000 | Yoon |
| 5,824,978 | A | 10/1998 | Karasik et al. | 6,090,107 | A | 7/2000 | Borgmeier et al. |
| 5,827,271 | A | 10/1998 | Buysse et al. | 6,096,037 | A * | 8/2000 | Mulier et al. ............ 606/49 |
| 5,827,279 | A | 10/1998 | Hughett et al. | 6,099,550 | A | 8/2000 | Yoon |
| 5,827,281 | A | 10/1998 | Levin | 6,102,909 | A | 8/2000 | Chen et al. |
| 5,827,323 | A | 10/1998 | Klieman et al. | 6,106,542 | A | 8/2000 | Toybin et al. |
| 5,827,548 | A | 10/1998 | Lavallee et al. | 6,110,171 | A | 8/2000 | Rydell |
| 5,833,690 | A | 11/1998 | Yates et al. | 6,113,596 | A | 9/2000 | Hooven et al. |
| 5,843,080 | A | 12/1998 | Fleenor et al. | 6,113,598 | A | 9/2000 | Baker |
| 5,849,022 | A | 12/1998 | Sakashita et al. | 6,117,158 | A | 9/2000 | Measamer et al. |
| 5,853,412 | A | 12/1998 | Mayenberger | 6,122,549 | A | 9/2000 | Sharkey et al. |
| 5,859,527 | A | 1/1999 | Cook | 6,123,701 | A | 9/2000 | Nezhat |
| 5,860,976 | A | 1/1999 | Billings et al. | H1904 | H | 10/2000 | Yates et al. |
| 5,876,401 | A | 3/1999 | Schulze et al. | 6,126,658 | A | 10/2000 | Baker |
| 5,876,412 | A | 3/1999 | Piraka | 6,126,665 | A | 10/2000 | Yoon |
| 5,882,567 | A | 3/1999 | Cavallaro et al. | 6,139,563 | A | 10/2000 | Cosgrove, III et al. |
| 5,891,141 | A | 4/1999 | Rydell | 6,143,005 | A | 11/2000 | Yoon et al. |
| 5,891,142 | A | 4/1999 | Eggers et al. | 6,152,923 | A | 11/2000 | Ryan |
| 5,893,863 | A | 4/1999 | Yoon | 6,162,220 | A | 12/2000 | Nezhat |
| 5,893,875 | A | 4/1999 | O'Connor et al. | 6,171,316 | B1 | 1/2001 | Kovac et al. |
| 5,893,877 | A | 4/1999 | Gampp, Jr. et al. | 6,174,309 | B1 | 1/2001 | Wrublewski et al. |
| 5,897,563 | A | 4/1999 | Yoon et al. | 6,178,628 | B1 | 1/2001 | Clemens et al. |
| 5,902,301 | A | 5/1999 | Olig | 6,179,834 | B1 | 1/2001 | Buysse et al. |
| 5,906,630 | A | 5/1999 | Anderhub et al. | 6,179,837 | B1 | 1/2001 | Hooven |
| 5,908,420 | A | 6/1999 | Parins et al. | 6,183,467 | B1 | 2/2001 | Shapeton et al. |
| 5,908,432 | A | 6/1999 | Pan | 6,187,003 | B1 | 2/2001 | Buysse et al. |
| 5,911,719 | A | 6/1999 | Eggers | 6,190,386 | B1 | 2/2001 | Rydell |
| 5,913,874 | A | 6/1999 | Berns et al. | 6,190,400 | B1 | 2/2001 | VanDeMoer et al. |
| 5,921,916 | A | 7/1999 | Aeikens et al. | 6,193,718 | B1 | 2/2001 | Kortenbach et al. |
| 5,921,984 | A | 7/1999 | Sutcu et al. | 6,206,876 | B1 | 3/2001 | Levine et al. |
| 5,925,043 | A | 7/1999 | Kumar et al. | 6,206,877 | B1 | 3/2001 | Kese et al. |
| 5,928,136 | A | 7/1999 | Barry | 6,206,893 | B1 | 3/2001 | Klein et al. |
| 5,935,126 | A | 8/1999 | Riza | 6,214,028 | B1 | 4/2001 | Yoon et al. |
| 5,941,869 | A | 8/1999 | Patterson et al. | 6,217,602 | B1 | 4/2001 | Redmon |
| 5,944,718 | A | 8/1999 | Austin et al. | 6,217,615 | B1 | 4/2001 | Sioshansi et al. |
| 5,951,546 | A | 9/1999 | Lorentzen | 6,221,039 | B1 | 4/2001 | Durgin et al. |
| 5,951,549 | A | 9/1999 | Richardson et al. | 6,223,100 | B1 | 4/2001 | Green |
| 5,954,720 | A | 9/1999 | Wilson et al. | 6,224,593 | B1 | 5/2001 | Ryan et al. |
| 5,954,731 | A | 9/1999 | Yoon | 6,224,614 | B1 | 5/2001 | Yoon |
| 5,954,733 | A | 9/1999 | Yoon | 6,228,080 | B1 | 5/2001 | Gines |
| 5,957,923 | A | 9/1999 | Hahnen et al. | 6,228,083 | B1 | 5/2001 | Lands et al. |
| 5,957,937 | A | 9/1999 | Yoon | 6,248,124 | B1 | 6/2001 | Pedros et al. |
| 5,960,544 | A | 10/1999 | Beyers | 6,248,944 | B1 | 6/2001 | Ito |
| 5,961,514 | A | 10/1999 | Long et al. | 6,261,307 | B1 | 7/2001 | Yoon et al. |
| 5,964,758 | A | 10/1999 | Dresden | 6,267,761 | B1 | 7/2001 | Ryan |
| 5,976,132 | A | 11/1999 | Morris | 6,270,497 | B1 | 8/2001 | Sekino et al. |
| 5,984,932 | A | 11/1999 | Yoon | 6,270,508 | B1 | 8/2001 | Klieman et al. |
| 5,984,938 | A | 11/1999 | Yoon | 6,273,887 | B1 | 8/2001 | Yamauchi et al. |
| 5,984,939 | A | 11/1999 | Yoon | 6,277,117 | B1 | 8/2001 | Tetzlaff et al. |
| 5,989,277 | A | 11/1999 | LeMaire, III et al. | 6,280,458 | B1 | 8/2001 | Boche et al. |
| 5,993,466 | A | 11/1999 | Yoon | 6,283,961 | B1 | 9/2001 | Underwood et al. |
| 5,993,467 | A | 11/1999 | Yoon | D449,886 | S | 10/2001 | Tetzlaff et al. |
| 5,997,565 | A | 12/1999 | Inoue | 6,298,550 | B1 | 10/2001 | Kirwan |
| 6,004,332 | A | 12/1999 | Yoon et al. | 6,302,424 | B1 | 10/2001 | Gisinger et al. |
| 6,004,335 | A | 12/1999 | Vaitekunas et al. | 6,319,262 | B1 | 11/2001 | Bates et al. |
| 6,010,516 | A | 1/2000 | Hulka et al. | 6,319,451 | B1 | 11/2001 | Brune |
| 6,017,358 | A | 1/2000 | Yoon et al. | 6,322,561 | B1 | 11/2001 | Eggers et al. |
| 6,021,693 | A | 2/2000 | Feng-Sing | 6,322,580 | B1 | 11/2001 | Kanner |
| 6,024,741 | A | 2/2000 | Williamson et al. | 6,325,795 | B1 | 12/2001 | Lindemann et al. |
| 6,024,743 | A | 2/2000 | Edwards | 6,334,860 | B1 | 1/2002 | Dorn |
| 6,024,744 | A | 2/2000 | Kese et al. | 6,334,861 | B1 | 1/2002 | Chandler et al. |
| 6,027,522 | A | 2/2000 | Palmer | 6,345,532 | B1 | 2/2002 | Coudray et al. |
| 6,030,384 | A | 2/2000 | Nezhat | 6,350,264 | B1 | 2/2002 | Hooven |
| 6,033,399 | A | 3/2000 | Gines | 6,352,536 | B1 | 3/2002 | Buysse et al. |
| 6,039,733 | A | 3/2000 | Buysse et al. | 6,358,249 | B1 | 3/2002 | Chen et al. |
| 6,041,679 | A | 3/2000 | Slater et al. | 6,358,259 | B1 | 3/2002 | Swain et al. |
| 6,050,996 | A | 4/2000 | Schmaltz et al. | 6,358,268 | B1 | 3/2002 | Hunt et al. |
| 6,053,914 | A | 4/2000 | Eggers et al. | 6,364,879 | B1 | 4/2002 | Chen et al. |
| 6,053,933 | A | 4/2000 | Balazs et al. | D457,958 | S | 5/2002 | Dycus et al. |
| D424,694 | S | 5/2000 | Tetzlaff et al. | D457,959 | S | 5/2002 | Tetzlaff et al. |
| D425,201 | S | 5/2000 | Tetzlaff et al. | 6,387,094 | B1 | 5/2002 | Eitenmuller |
| 6,059,782 | A | 5/2000 | Novak et al. | 6,391,035 | B1 | 5/2002 | Appleby et al. |
| 6,066,139 | A | 5/2000 | Ryan et al. | 6,398,779 | B1 | 6/2002 | Buysse et al. |
| 6,074,386 | A | 6/2000 | Goble et al. | 6,402,747 | B1 | 6/2002 | Lindemann et al. |
| 6,077,287 | A | 6/2000 | Taylor et al. | 6,409,728 | B1 | 6/2002 | Ehr et al. |
| 6,080,180 | A | 6/2000 | Yoon et al. | H2037 | H | 7/2002 | Yates et al. |
| RE36,795 | E | 7/2000 | Rydell | 6,419,675 | B1 | 7/2002 | Gallo, Sr. |
| 6,083,223 | A | 7/2000 | Baker | 6,425,896 | B1 | 7/2002 | Baltschun et al. |

| | | | |
|---|---|---|---|
| 6,432,112 B2 | 8/2002 | Brock et al. | |
| 6,440,144 B1 | 8/2002 | Bacher | |
| 6,443,952 B1 | 9/2002 | Mulier et al. | |
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 | 10/2002 | Morgan et al. | |
| 6,461,368 B2 | 10/2002 | Fogarty et al. | |
| 6,464,701 B1 | 10/2002 | Hooven et al. | |
| 6,464,702 B2 | 10/2002 | Schulze et al. | |
| 6,464,704 B2 | 10/2002 | Schmaltz et al. | |
| 6,485,489 B2 | 11/2002 | Teirstein et al. | |
| 6,488,680 B1 * | 12/2002 | Francischelli et al. | 606/41 |
| 6,494,888 B1 | 12/2002 | Laufer et al. | |
| 6,500,176 B1 | 12/2002 | Truckai et al. | |
| 6,506,196 B1 | 1/2003 | Laufer | |
| 6,508,815 B1 | 1/2003 | Strul et al. | |
| 6,511,480 B1 | 1/2003 | Tetzlaff et al. | |
| 6,514,215 B1 | 2/2003 | Ouchi | |
| 6,514,252 B2 | 2/2003 | Nezhat et al. | |
| 6,517,539 B1 | 2/2003 | Smith et al. | |
| 6,527,771 B1 | 3/2003 | Weadock et al. | |
| 6,533,784 B2 | 3/2003 | Truckai et al. | |
| 6,545,239 B2 | 4/2003 | Spedale et al. | |
| 6,558,385 B1 | 5/2003 | McClurken et al. | |
| 6,562,037 B2 | 5/2003 | Paton et al. | |
| 6,569,105 B1 | 5/2003 | Kortenbach et al. | |
| 6,582,450 B2 | 6/2003 | Ouchi | |
| 6,585,735 B1 | 7/2003 | Frazier et al. | |
| 6,602,252 B2 | 8/2003 | Mollenauer | |
| 6,605,790 B2 | 8/2003 | Yoshida | |
| 6,616,658 B2 | 9/2003 | Ineson | |
| 6,616,661 B2 | 9/2003 | Wellman et al. | |
| 6,620,161 B2 | 9/2003 | Schulze et al. | |
| 6,620,184 B2 | 9/2003 | De Laforcade et al. | |
| 6,626,901 B1 | 9/2003 | Treat et al. | |
| 6,638,287 B2 | 10/2003 | Danitz et al. | |
| 6,641,595 B1 | 11/2003 | Moran et al. | |
| 6,652,514 B2 | 11/2003 | Ellman et al. | |
| 6,652,521 B2 | 11/2003 | Schulze | |
| 6,656,175 B2 | 12/2003 | Francischelli et al. | |
| 6,656,177 B2 | 12/2003 | Truckai et al. | |
| 6,660,072 B2 | 12/2003 | Chatterjee | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,669,696 B2 | 12/2003 | Bacher et al. | |
| 6,673,092 B1 | 1/2004 | Bacher | |
| 6,676,660 B2 | 1/2004 | Wampler et al. | |
| 6,676,676 B2 | 1/2004 | Danitz et al. | |
| 6,679,882 B1 | 1/2004 | Kornerup | |
| 6,682,527 B2 | 1/2004 | Strul | |
| 6,682,528 B2 | 1/2004 | Frazier et al. | |
| 6,685,724 B1 | 2/2004 | Haluck | |
| 6,689,131 B2 | 2/2004 | McClurken | |
| 6,692,445 B2 | 2/2004 | Roberts et al. | |
| 6,693,246 B1 | 2/2004 | Rudolph et al. | |
| 6,695,840 B2 | 2/2004 | Schulze | |
| 6,702,810 B2 | 3/2004 | McClurken et al. | |
| 6,723,092 B2 | 4/2004 | Brown et al. | |
| 6,726,068 B2 | 4/2004 | Miller | |
| 6,726,694 B2 | 4/2004 | Blatter et al. | |
| 8,726,686 | 4/2004 | Buysse et al. | |
| 6,733,498 B2 | 5/2004 | Paton et al. | |
| 6,736,813 B2 | 5/2004 | Yamauchi et al. | |
| 6,743,229 B2 | 6/2004 | Buysse et al. | |
| 6,743,230 B2 | 6/2004 | Lutze et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,756,553 B1 | 6/2004 | Yamaguchi et al. | |
| 6,757,977 B2 | 7/2004 | Dambal et al. | |
| D493,888 S | 8/2004 | Reschke | |
| 6,770,072 B1 * | 8/2004 | Truckai et al. | 606/52 |
| 6,773,409 B2 | 8/2004 | Truckai et al. | |
| 6,773,432 B1 | 8/2004 | Clayman et al. | |
| 6,773,434 B2 | 8/2004 | Ciarrocca | |
| 6,773,441 B1 | 8/2004 | Laufer et al. | |
| 6,775,575 B2 | 8/2004 | Bommannan et al. | |
| 6,776,780 B2 | 8/2004 | Mulier et al. | |
| 6,786,905 B2 | 9/2004 | Swanson et al. | |
| 6,790,217 B2 | 9/2004 | Schulze et al. | |
| 6,796,981 B2 | 9/2004 | Wham et al. | |
| D496,997 S | 10/2004 | Dycus et al. | |
| 6,800,825 B1 | 10/2004 | Sasaki et al. | |
| 6,802,843 B2 | 10/2004 | Truckai et al. | |
| 6,808,525 B2 | 10/2004 | Latterell et al. | |
| D499,181 S | 11/2004 | Dycus et al. | |
| 6,818,000 B2 | 11/2004 | Muller et al. | |
| 6,821,285 B2 | 11/2004 | Laufer et al. | |
| 6,835,200 B2 | 12/2004 | Laufer et al. | |
| 6,857,357 B2 | 2/2005 | Fujii | |
| 6,860,880 B2 | 3/2005 | Treat et al. | |
| 6,887,240 B1 | 5/2005 | Lands et al. | |
| 6,889,116 B2 | 5/2005 | Jinno | |
| 6,914,201 B2 | 7/2005 | Van Vooren et al. | |
| 6,926,716 B2 | 8/2005 | Baker et al. | |
| 6,929,644 B2 | 8/2005 | Truckai et al. | |
| 6,932,816 B2 | 8/2005 | Phan | |
| 6,934,134 B2 | 8/2005 | Mori et al. | |
| 6,936,061 B2 | 8/2005 | Sasaki | |
| 8,932,810 | 8/2005 | Ryan | |
| D509,297 S | 9/2005 | Wells | |
| 6,942,662 B2 | 9/2005 | Goble et al. | |
| 6,943,311 B2 | 9/2005 | Miyako | |
| 6,953,430 B2 | 10/2005 | Kidooka | |
| 6,953,461 B2 * | 10/2005 | McClurken et al. | 606/51 |
| 6,958,070 B2 | 10/2005 | Witt et al. | |
| 6,960,210 B2 | 11/2005 | Lands et al. | |
| 6,964,662 B2 | 11/2005 | Kidooka | |
| 6,966,907 B2 | 11/2005 | Goble | |
| 6,972,017 B2 | 12/2005 | Smith et al. | |
| 6,977,495 B2 | 12/2005 | Donofrio | |
| 6,979,786 B2 | 12/2005 | Aukland et al. | |
| 6,981,628 B2 | 1/2006 | Wales | |
| 6,987,244 B2 | 1/2006 | Bauer | |
| 6,994,707 B2 | 2/2006 | Ellman et al. | |
| 6,994,709 B2 | 2/2006 | Iida | |
| 6,997,931 B2 | 2/2006 | Sauer et al. | |
| 7,001,381 B2 | 2/2006 | Harano et al. | |
| 7,011,657 B2 | 3/2006 | Truckai et al. | |
| 7,033,354 B2 | 4/2006 | Keppel | |
| 7,033,356 B2 | 4/2006 | Latterell et al. | |
| 7,041,102 B2 | 5/2006 | Truckai et al. | |
| 7,044,948 B2 | 5/2006 | Keppel | |
| 7,052,489 B2 | 5/2006 | Griego et al. | |
| 7,052,496 B2 | 5/2006 | Yamauchi | |
| 7,063,715 B2 | 6/2006 | Onuki et al. | |
| D525,361 S | 7/2006 | Hushka | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,083,620 B2 | 8/2006 | Jahns et al. | |
| 7,087,051 B2 | 8/2006 | Bourne et al. | |
| 7,087,054 B2 | 8/2006 | Truckai et al. | |
| 7,090,673 B2 | 8/2006 | Dycus et al. | |
| 7,090,689 B2 | 8/2006 | Nagase et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,103,947 B2 | 9/2006 | Sartor et al. | |
| 7,107,124 B2 | 9/2006 | Green | |
| 7,112,199 B2 | 9/2006 | Cosmescu | |
| D531,311 S | 10/2006 | Guerra et al. | |
| 7,115,123 B2 | 10/2006 | Knowlton et al. | |
| 7,118,570 B2 | 10/2006 | Tetzlaff et al. | |
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |
| 7,135,020 B2 | 11/2006 | Lawes et al. | |
| D533,942 S | 12/2006 | Kerr et al. | |
| 7,145,757 B2 | 12/2006 | Shea et al. | |
| 7,147,638 B2 | 12/2006 | Chapman et al. | |
| 7,150,097 B2 | 12/2006 | Sremcich et al. | |
| 7,150,749 B2 | 12/2006 | Dycus et al. | |

| | | |
|---|---|---|
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109863 A1 | 6/2003 | Francischelli |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0144652 A1 | 7/2003 | Baker |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0186348 A1 | 9/2004 | Kidooka |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |

| | | |
|---|---|---|
| 2006/0173452 A1 | 8/2006 | Buysse et al. |
| 2006/0189980 A1 | 8/2006 | Johnson et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19738457 | 3/1999 |
| DE | 19751108 | 5/1999 |
| DE | 19738457 | 1/2009 |
| EP | 0364216 A1 | 4/1990 |
| EP | 0467501 | 1/1992 |
| EP | 0518230 A1 | 12/1992 |
| EP | 0 541 930 B1 | 5/1993 |
| EP | 0572131 | 12/1993 |
| EP | 0584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 0853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |

| | | |
|---|---|---|
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO03/061500 | 7/2003 |
| WO | WO 03061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectormy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery"ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle at al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
International Search Report EP08002692.5 Dated: Dec. 12, 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

Section AA

VESSEL SEALING INSTRUMENT WITH ELECTRICAL CUTTING MECHANISM

CROSS REFERENCE TO RELATED APPLICATIONS

This application claims the benefit of and is a continuation-in-part of U.S. patent application Ser. No. 11/418,876, filed on May 5, 2006 entitled "VESSEL SEALING INSTRUMENT WITH ELECTRICAL CUTTING MECHANISM", now U.S. Pat. No. 7,270,664, which is a continuation-in-part of U.S. application Ser. No, 10/932,612, filed on Sep. 2, 2004, entitled "VESSEL SEALING INSTRUMENT WITH ELECTRICAL CUTTING MECHANISM", now U.S. Pat. No. 7,276,068, which is a continuation-in-part of PCT application Ser. No. PCT/US03/28539 filed on Sep. 11, 2003 entitled "ELECTRODE ASSEMBLY FOR SEALING AND CUTTING TISSUE AND METHOD FOR PERFORMING SAME", which claims the benefit of and priority to U.S. Provisional Application Ser. No. 60/416,064 filed on Oct. 4, 2002 entitled "ELECTRODE ASSEMBLY FOR SEALING AND CUTTING TISSUE AND METHOD FOR PERFORMING SAME", all of which are herein incorporated by reference in their entirety.

BACKGROUND

1. Technical Field

The present disclosure relates to a forceps used for both endoscopic and open surgical procedures that includes an electrode assembly that allows a user to selectively seal and/or cut tissue. More particularly, the present disclosure relates to a forceps that includes a first set of electrically conductive surfaces that applies a unique combination of mechanical clamping pressure and electrosurgical energy to effectively seal tissue and a second set of electrically conductive surfaces that is selectively energizable to sever tissue between sealed tissue areas.

2. Background of the Invention

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can either cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing is a recently-developed technology that utilizes a unique combination of radiofrequency energy, clamping pressure and precise control of gap distance (i.e., distance between opposing jaw members when closed about tissue) to effectively seal or fuse tissue between two opposing jaw members or sealing plates. Vessel or tissue sealing is more than "cauterization", which involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

To effectively seal tissue or vessels, especially thick tissue and large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to oppose the walls of the vessel; to reduce the tissue impedance to a low enough value that allows enough electrosurgical energy through the tissue; to overcome the forces of expansion during tissue heating; and to contribute to the end tissue thickness, which is an indication of a good seal. It has been determined that a typical instrument gap is optimum between about 0.001 and about 0.006 inches. Below this range, the seal may shred or tear and the jaws may "short circuit" and not deliver the proper energy to the tissue. Above this range, thin or small tissue structures may not be properly or effectively sealed.

With respect to smaller vessels, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Typically, and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. This additional step may be both time consuming (particularly when sealing a significant number of vessels) and may contribute to imprecise separation of the tissue along the sealing line due to the misalignment or misplacement of the severing instrument along the center of the tissue seal.

SUMMARY

The present disclosure relates to an end effector assembly for use with an instrument for sealing and cutting vessels and/or tissue. An end effector assembly for use with an instrument for sealing vessels and cutting vessels includes a pair of opposing first and second jaw members which are movable relative to one another from a first spaced apart position to a second position for grasping tissue therebetween. Each jaw member includes an electrically conductive tissue contacting surface connected to an electrosurgical energy source. At least one of the jaw members includes an electrically conductive cutting element disposed within an insulator defined in the jaw member. A rigid structural support is included which is configured to support the electrically conductive tissue sealing surface and includes at least one flow channel defined therein.

In one embodiment of the present disclosure a layer of insulative material is included which is disposed between the electrically conductive tissue sealing surface and the rigid structural support. The rigid structural support or structural backing may include perforations. The insulator may be located between the perforations of the structural backing.

In yet another embodiment of the present disclosure the electrically conductive cutting element may include at least one mechanically interfacing surface configured to mate with the insulative material to retain the electrically conductive cutting element within the insulator.

In one embodiment according to the present disclosure the electrically conductive tissue sealing surfaces are photochemically etched or formed from a stamping process. At least one of the insulators may be configured to at least partially extend to a position which is at least substantially flush with the cutting element.

A second electrically conductive cutting element may be provided which is disposed within the insulator of the second jaw member. The second electrically conductive cutting element may be disposed in generally opposing relation to the first electrically conductive cutting element.

In yet another embodiment of the present disclosure an end effector assembly for use with an instrument for sealing and cutting vessels and/or tissue is provided. The assembly includes a pair of opposing first and second jaw members at least one of which being movable relative to the other from a first position wherein the jaw members are disposed in spaced relation relative to one another to a second position wherein the jaw members cooperate to grasp tissue therebetween. Each jaw member includes a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal. An insulator is disposed between each pair of electrically conductive sealing surfaces. The first jaw member includes an electrically conductive cutting element disposed within the insulator of the first jaw member, the electrically conductive cutting element disposed in general vertical registration to the insulator on the second jaw member. The assembly includes at least one tissue tensioning mechanism configured to provide tension to tissue held between jaw members.

In another embodiment of the present disclosure a slot defined within the second jaw member is included, the slot configured to receive the electrically conductive cutting element and create tension upon tissue.

In yet another embodiment of the present disclosure the electrically conductive tissue sealing surfaces are disposed in an angular relationship relative to one another, and may be constructed of an expandable material (e.g., a shape memory alloy such as shaped memory alloy (SMA and/or Nitinol) or may include a spring-like device.

In yet another embodiment of the present disclosure an end effector assembly for use with an instrument for sealing, coagulating and/or cutting vessels and/or tissue is provided. The assembly includes a pair of opposing first and second jaw members at least one of which being movable relative to the other from a first position wherein the jaw members are disposed in spaced relation relative to one another to a second position wherein the jaw members cooperate to grasp tissue therebetween. Each jaw member includes a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal. An insulator support element configured to support each electrically conductive sealing surface is disposed between each pair of electrically conductive sealing surfaces. At least one jaw member includes an electrically conductive cutting element disposed within at least one insulative support element of a jaw member. Moreover, each jaw member includes at least one channel configured to pass fluid adjacent to the electrically conductive cutting element defined within at least one of the insulative support elements.

In yet another embodiment, the channel further includes at least one port configured to at least deliver fluid through the port. The fluid can be at least one of a conductive fluid, non-conductive fluid, and combinations thereof. In some embodiments, the fluid is at least one of conductive fluids such as aqueous solutions, saline solutions, salt solutions, electrolyte containing solutions, and combinations thereof. In some embodiments, the fluid is a non-conductive fluid is at least one of aqueous solutions, a solution having 1.5% glycine, a solution having 3% sorbitol, a solution having 5% mannitol, a sterile water solution, and combinations thereof.

In yet another embodiment, the channel is in communication with at least one pump.

In yet another embodiment, one jaw member is configured to include one or more sensors configured to monitor the conductivity of tissue disposed between the jaws.

In yet another embodiment, one or more jaw members includes a rigid structural support disposed within the insulative support of at least one jaw member having the electrically conductive cutting element configured in general vertical registration with the electrically conductive tissue sealing surface. Optionally, the channel can pass through at least a portion of the rigid structural support. In some embodiments, a layer of insulative material is disposed between the electrically conductive tissue sealing surfaces and the rigid structural support. In some embodiments, a channel passes through at least a portion of the layer of insulative material disposed between the electrically conductive tissue sealing surfaces and the channel passes through at least a portion of the rigid structural support. The channel further includes at least one port configured to at least deliver fluid through the port. The fluid can be at least one of a conductive fluid, non-conductive fluid, and combinations thereof. In some embodiments, the fluid is at least one of conductive fluids such as aqueous solutions, saline solutions, salt solutions, electrolyte containing solutions, and combinations thereof. In some embodiments, the fluid is a non-conductive fluid is at least one of aqueous solutions, a solution having 1.5% glycine, a solution having 3% sorbitol, a solution having 5% mannitol, a sterile water solution, and combinations thereof. In some embodiments, the channel is in communication with at least one pump.

In yet another embodiment, the electrically conductive tissue sealing surfaces are formed onto the insulative support element by a stamping process.

In yet another embodiment at least one of the insulators is configured to at least partially extend to a position which is at least substantially flush with the cutting element.

In yet another embodiment, a second electrically conductive cutting element is disposed within the insulative material of the opposing jaw member, the second electrically conductive cutting element generally opposing the first electrically conductive cutting element.

In yet another embodiment of the present disclosure an end effector assembly for use with an instrument for sealing, coagulating and/or cutting vessels and/or tissue is provided. The assembly includes a pair of opposing first and second jaw members at least one of which being movable relative to the other from a first position wherein the jaw members are disposed in spaced relation relative to one another to a second position wherein the jaw members cooperate to grasp tissue therebetween. Each jaw member includes a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal. An insulator support element configured to support each electrically conductive sealing surface is disposed between each pair of electrically conductive sealing surfaces. The first jaw member may include an electrically conductive cutting element disposed within the insulator of the first jaw member, the electrically conductive cutting element disposed in general vertical registration to the insulator on the second jaw member. Furthermore, at least one channel is defined through the insulator, the channel configured to provide fluid to tissue held between jaw members. Moreover, the device may include at least one tissue tensioning mechanism configured to provide tension to tissue held between jaw members.

In yet another embodiment, the electrically conductive tissue sealing surfaces are disposed in an angular relationship relative to one another. These electrically conductive cutting elements may be constructed of an expandable material. The expandable material may be a shaped memory alloy (SMA).

In yet another embodiment of the present disclosure a method of modifying the conductivity of tissue during an electrosurgical procedure is provided. The method may include providing an end effector assembly in accordance with the present disclosure such an end effector assembly for use with an instrument for sealing, coagulating and/or cutting vessels and/or tissue. The assembly includes a pair of opposing first and second jaw members at least one of which being movable relative to the other from a first position wherein the jaw members are disposed in spaced relation relative to one another to a second position wherein the jaw members cooperate to grasp tissue therebetween. Each jaw member includes a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal. An insulator support element configured to support each electrically conductive sealing surface is disposed between each pair of electrically conductive sealing surfaces. At least one jaw member includes an electrically conductive cutting element disposed within at least one insulative support element of the jaw members. Moreover, each jaw member includes at least one channel configured to move fluid adjacent to the electrically conductive cutting element defined within at least one of the insulative support elements. The method further includes the step of selectively adjusting the amount of fluid adjacent to the tissue during an electrosurgical procedures.

The methods in accordance with the present disclosure may further include the step of selectively adjusting the amount of fluid by adding fluid to the tissue. Furthermore, the methods in accordance with the present disclosure may further include the step of selectively adjusting the amount of fluid by removing fluid from the tissue. The methods in accordance with the present disclosure may further include providing fluid that may be at least one of a conductive fluid, a non-conductive fluid, and combinations thereof. In some embodiments, the fluid may be at least one of aqueous solutions, saline solutions, salt solutions, electrolyte containing solutions, and combinations thereof. In some embodiments, the non-conductive fluid may be at least one of aqueous solutions, a solution having 1.5% glycine, a solution having 3% sorbitol, a solution having 5% mannitol, a solution of sterile water, and combinations thereof.

BRIEF DESCRIPTION OF THE DRAWINGS

Various embodiments of the subject instrument are described herein with reference to the drawings wherein.

DETAILED DESCRIPTION

Figure 1A:
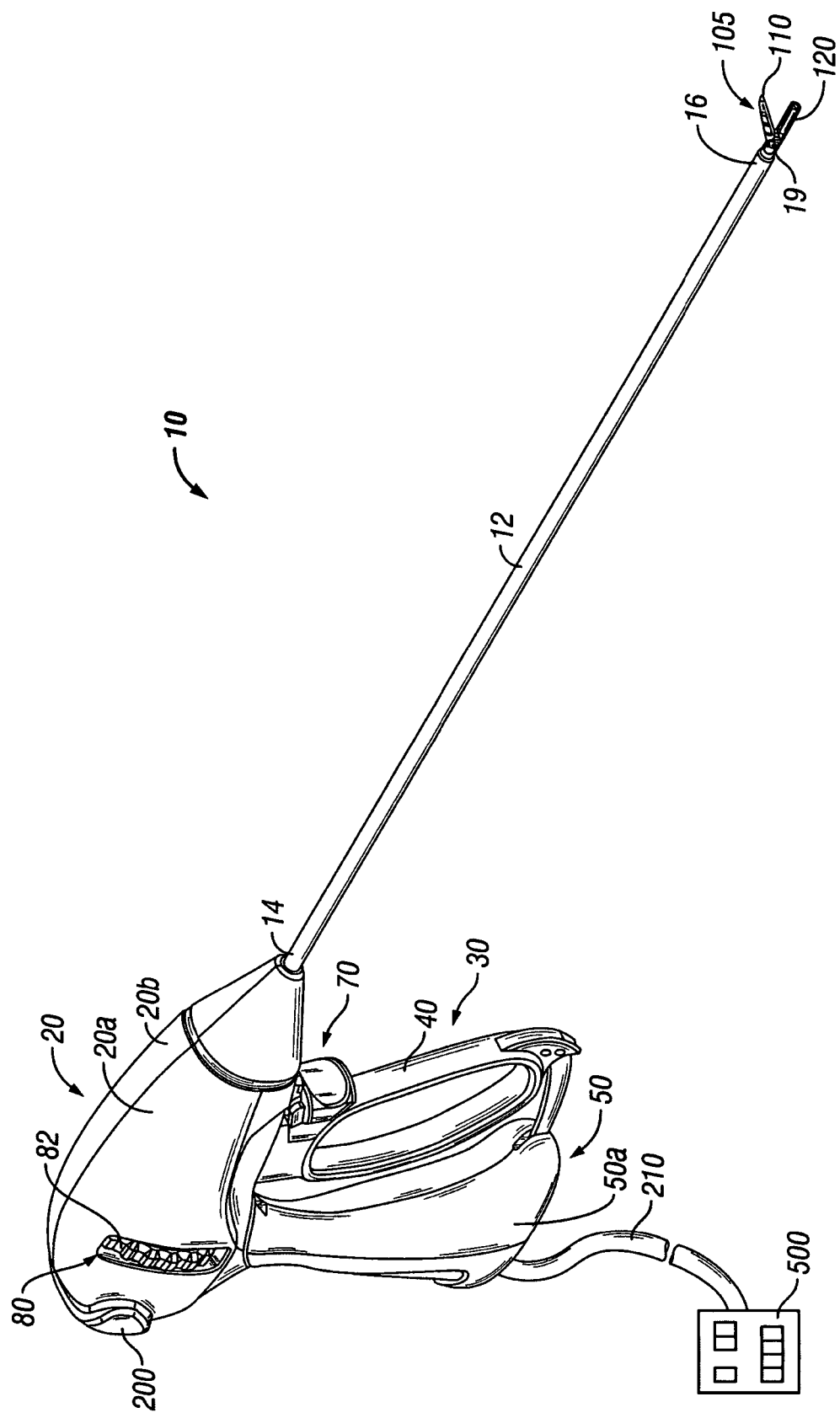
FIG. 1A is a right, perspective view of an endoscopic bipolar forceps having a housing, a shaft and a pair of jaw members affixed to a distal end thereof, the jaw members including an electrode assembly disposed therebetween.

For the purposes herein, vessel/tissue cutting or vessel/tissue division is believed to occur when heating of the vessel/tissue leads to expansion of intracellular and/or extra-cellular fluid, which may be accompanied by cellular vaporization, desiccation, fragmentation, collapse and/or shrinkage along a so-called "cut zone" in the vessel/tissue. By focusing the electrosurgical energy and heating in the cut zone, the cellular reactions are localized creating a fissure. Localization is achieved by regulating the vessel/tissue condition and energy delivery, which may be controlled by utilizing one or more of the various geometrical electrode and insulator configurations described herein. The cut process may also be controlled by utilizing a generator and feedback algorithm (and one or more of the herein described geometrical configurations of the electrode and insulator assemblies), which increases the localization and maximizes the so-called "cutting effect".

For example, the below described factors may contribute and/or enhance vessel/tissue division using electrosurgical energy. Each of the factors described below may be employed individually or in any combination to achieve a desired cutting effect. For the purposes herein the term "cut effect" or "cutting effect" refers to the actual division of tissue by one or more of the electrical or electromechanical methods or mechanisms described below. The term "cutting zone" or "cut zone" refers to the region of vessel/tissue where cutting will take place. The term "cutting process" refers to steps that are implemented before, during and/or after vessel/tissue division that tend to influence the vessel/tissue as part of achieving the cut effect.

For the purposes herein the terms "tissue" and "vessel" may be used interchangeably since it is believed that the present disclosure may be employed to seal and cut tissue or seal and cut vessels utilizing the same inventive principles described herein.

It is believed that the following factors either alone or in combination, play an important role in dividing tissue:

Localizing or focusing electrosurgical energy in the cut zone during the cutting process while minimizing energy effects to surrounding tissues;

Focusing the power density in the cut zone during the cutting process;

Creating an area of increased temperature in the cut zone during the cutting process (e.g., heating that occurs within the tissue or heating the tissue directly with a heat source);

Pulsing the energy delivery to influence the tissue in or around the cut zone. "Pulsing" involves as a combination of an "on" time and "off" time during which the energy is applied and then removed repeatedly at any number of intervals for any amount of time. The pulse "on" and "off" time may vary between pulses. The pulse "on" typically refers to a state of higher power delivery and pulse "off" typically refers to a state of lower power delivery;

Spiking the energy delivery creates a momentary condition of high energy application with an intent to influence the tissue in or around the cut zone during the cut process. The momentary condition may be varied to create periods of high energy application;

Conditioning the tissue before or during the cutting process to create more favorable tissue conditions for cutting. This includes tissue pre-heating before the cutting processes and tissue rehydration during the cutting process;

Controlling the tissue volume in or around the cut zone to create more favorable conditions for tissue cutting;

Controlling energy and power delivery to allow vaporization to enhance and or contribute to the cutting process. For example, controlling the energy delivery to vaporize both intracellular and/or extracellular fluids and/or other cellular materials and foreign fluids within the cut zone;

Fragmenting the tissue or cellular material during the cutting process to enhance tissue division in the cut zone;

Melting or collapsing the tissue or cellular material during the cutting process to enhance tissue division in the cut zone. For example, melting the tissue to create internal stress within the tissue to induce tissue tearing;

Controlling tissue temperature, arcing, power density and/or current density during the cutting process to enhance tissue division in the cut zone;

Applying various mechanical elements to the tissue, such as pressure, tension and/or stress (either internally or externally) to enhance the cutting process;

Utilizing various other tissue treatments before or during the cutting process to enhance tissue cutting, e.g., tissue sealing, cauterization and/or coagulation; and Movement/motion of one or more electrically charged or insulative members.

Many of the electrode assemblies described herein employ one or more of the above-identified factors for enhancing tissue division. For example, many of the electrode assemblies described herein utilize various geometrical configurations of electrodes, cutting elements, insulators, partially conductive materials and semiconductors to produce or enhance the cutting effect. In addition, by controlling or regulating the electrosurgical energy from the generator in any of the ways described above, tissue cutting may be initiated, enhanced or facilitated within the tissue cutting zone. For example, the geometrical configuration of the electrodes and insulators may be configured to produce a so-called "cut effect", which may be directly related to the amount of vaporization or fragmentation at a point in the tissue or the power density, temperature density and/or mechanical stress applied to a point in the tissue. The geometry of the electrodes may be configured such that the surface area ratios between the electrical poles focus electrical energy at the tissue. Moreover, the geometrical configurations of the electrodes and insulators may be designed such that they act like electrical (or thermal) sinks or insulators to influence the heat effect within and around the tissue during the sealing or cutting processes.

Figure 1B:
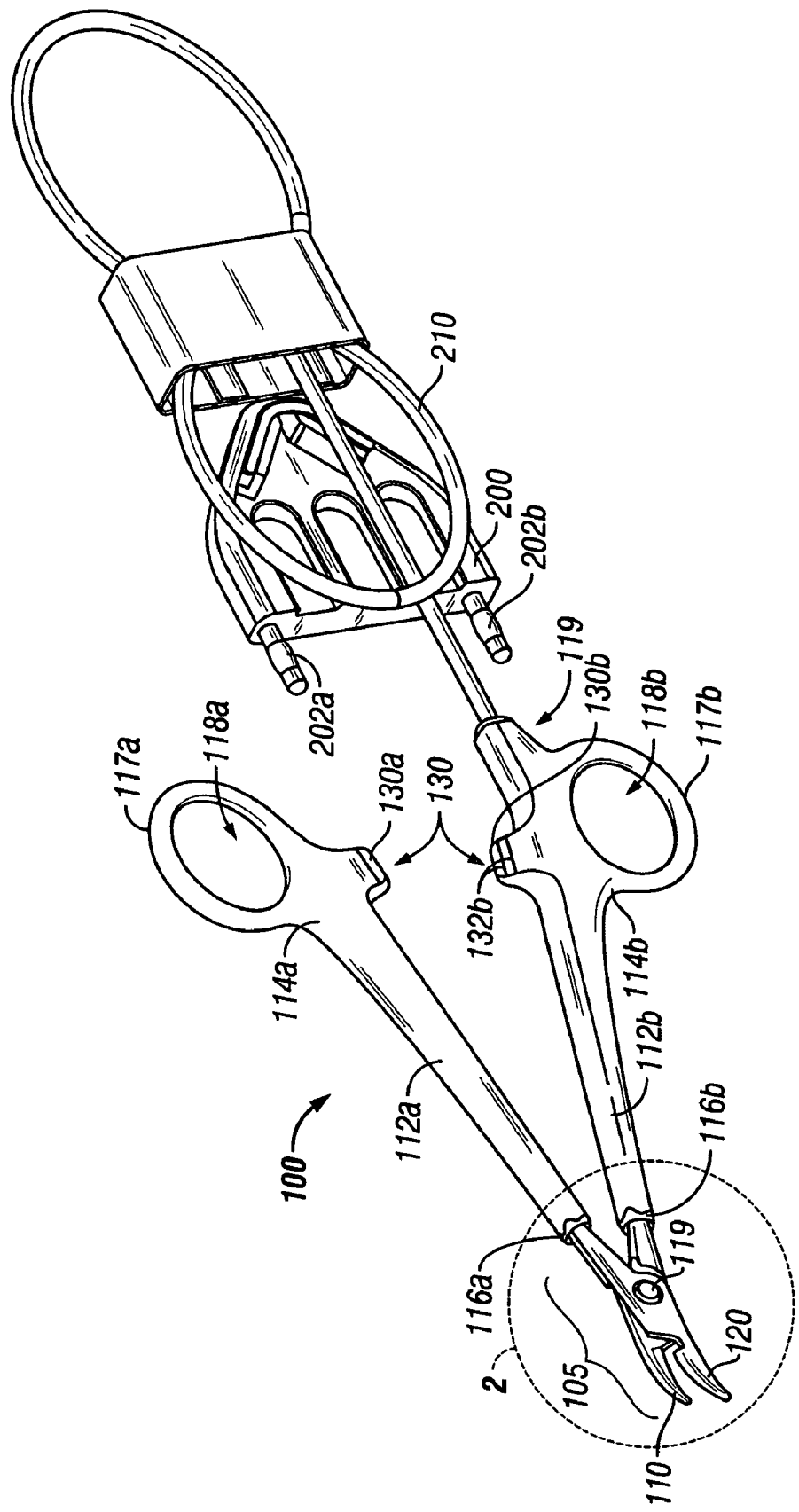
FIG. 1B is a left, perspective view of an open bipolar forceps showing a pair of first and second shafts each having a jaw member affixed to a distal end thereof with an electrode assembly disposed therebetween.

Referring now to FIGS. 1A and 1B, FIG. 1A depicts a bipolar forceps 10 for use in connection with endoscopic surgical procedures and FIG. 1B depicts an open forceps 100 contemplated for use in connection with traditional open surgical procedures. For the purposes herein, either an endoscopic instrument or an open instrument may be utilized with the electrode assembly described herein. Different electrical and mechanical connections and considerations may apply to each particular type of instrument; however, the novel aspects with respect to the electrode assembly and its operating characteristics remain generally consistent with respect to both the open or endoscopic designs.

FIG. 1A shows a bipolar forceps 10 for use with various endoscopic surgical procedures and generally includes a housing 20, a handle assembly 30, a rotating assembly 80, a switch assembly 70 and an electrode assembly 105 having opposing jaw members 110 and 120 that mutually cooperate to grasp, seal and divide tubular vessels and vascular tissue. More particularly, forceps 10 includes a shaft 12 that has a distal end 16 dimensioned to mechanically engage the electrode assembly 105 and a proximal end 14 that mechanically engages the housing 20. The shaft 12 may include one or more known mechanically engaging components that are designed to securely receive and engage the electrode assembly 105 such that the jaw members 110 and 120 are pivotable relative to one another to engage and grasp tissue therebetween.

The proximal end 14 of shaft 12 mechanically engages the rotating assembly 80 (not shown) to facilitate rotation of the electrode assembly 105. In the drawings and in the descriptions that follow, the term "proximal", as is traditional, will refer to the end of the forceps 10 that is closer to the user, while the term "distal" will refer to the end that is further from the user. Details relating to the mechanically cooperating components of the shaft 12 and the rotating assembly 80 are described in commonly-owned U.S. patent application Ser. No. 10/460,926 entitled "VESSEL SEALER AND DIVIDER FOR USE WITH SMALL TROCARS AND CANNULAS" filed on Jun. 13, 2003 the entire contents of which are incorporated by reference herein.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 105 as explained in more detail below. Movable handle 40 and switch assembly 70 are of unitary construction and are operatively connected to the housing 20 and the fixed handle 50 during the assembly process. Housing 20 is constructed from two component halves 20a and 20b, which are assembled about the proximal end of shaft 12 during assembly. Switch assembly is configured to selectively provide electrical energy to the electrode assembly 105.

As mentioned above, electrode assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 1B, an open forceps 100 includes a pair of elongated shaft portions 112a and 112b each having a proximal end 114a and 114b, respectively, and a distal end 116a and 116b, respectively. The forceps 100 includes jaw members 120 and 110 that attach to distal ends 116a and 116b of shafts 112a and 112b, respectively. The jaw members 110 and 120 are connected about pivot pin 119, which allows the jaw members 110 and 120 to pivot relative to one another from the first to second positions for treating tissue. The electrode assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/116,824, 10/284,562 10/472,295, 10/116,944, 10/179,863 and 10/369,894, the contents of all of which are hereby incorporated by reference herein.

Each shaft 112a and 112b includes a handle 117a and 117b disposed at the proximal end 114a and 114b thereof that each define a finger hole 118a and 118b, respectively, therethrough for receiving a finger of the user. As can be appreciated, finger holes 118a and 118b facilitate movement of the shafts 112a and 112b relative to one another, which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 may be included for selectively locking the jaw members 110 and 120 relative to one another at various positions during pivoting.

More particularly, the ratchet 130 includes a first mechanical interface 130a associated with shaft 112a and a second mating mechanical interface associated with shaft 112b. Each position associated with the cooperating ratchet interfaces 130a and 130b holds a specific, i.e., constant, strain energy in the shaft members 112a and 112b, which, in turn, transmits a specific closing force to the jaw members 110 and 120. The ratchet 130 may include graduations or other visual markings that enable the user to easily and quickly ascertain and control the amount of closure force desired between the jaw members 110 and 120.

As best seen in FIG. 1B, forceps 100 also includes an electrical interface or plug 200 that connects the forceps 100 to a source of electrosurgical energy, e.g., an electrosurgical generator (not explicitly shown). Plug 200 includes at least two prong members 202a and 202b that are dimensioned to mechanically and electrically connect the forceps 100 to the electrosurgical generator 500 (See FIG. 1A). An electrical cable 210 extends from the plug 200 and securely connects the cable 210 to the forceps 100. Cable 210 is internally divided within the shaft 112b to transmit electrosurgical energy through various electrical feed paths to the electrode assembly 105.

One of the shafts, e.g. 112b, includes a proximal shaft connector/flange 119 that is designed to connect the forceps 100 to a source of electrosurgical energy such as an electrosurgical generator 500. More particularly, flange 119 mechanically secures electrosurgical cable 210 to the forceps 100 such that the user may selectively apply electrosurgical energy as needed.

Figure 2:
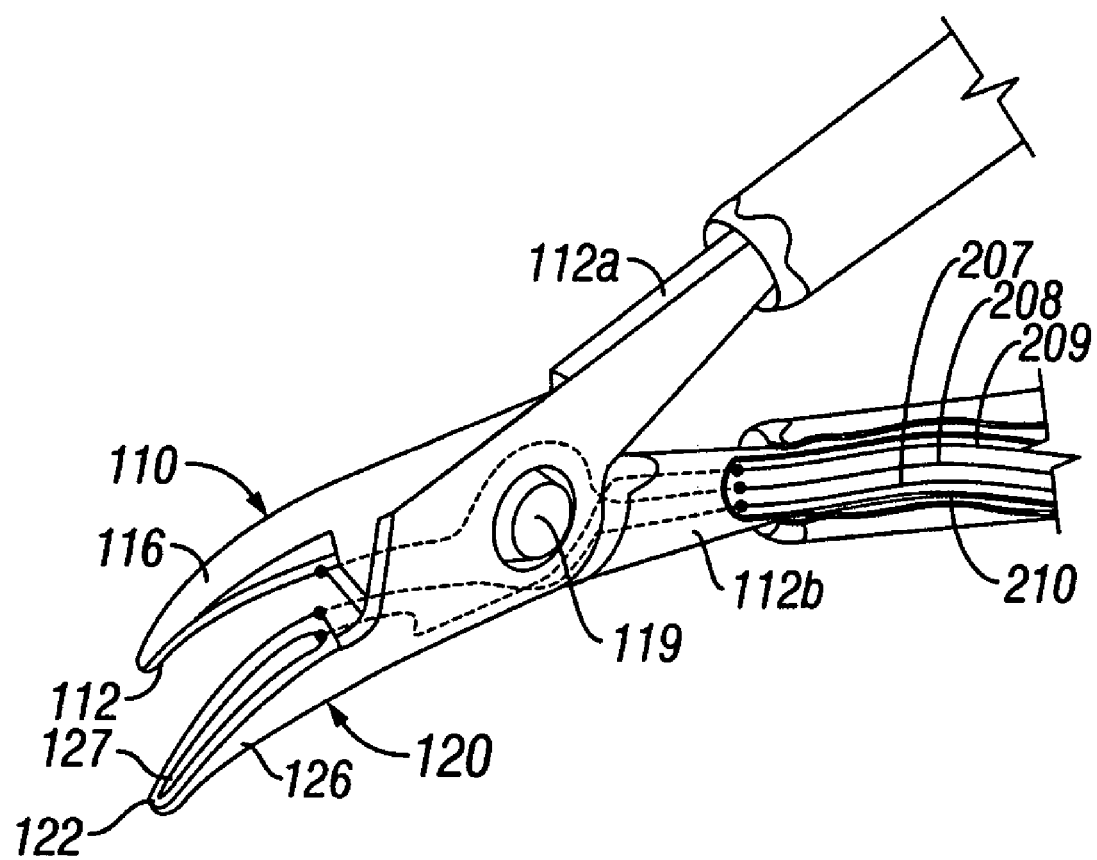
FIG. 2 is an enlarged view of the area of detail of FIG. 1B

As best shown in the schematic illustration of FIG. 2, the jaw members 110 and 120 of both the endoscopic version of FIG. 1A and the open version of FIG. 1B are generally symmetrical and include similar component features that cooperate to permit facile rotation about pivot 19, 119 to effect the grasping and sealing of tissue. Each jaw member 110 and 120 includes an electrically conductive tissue contacting surface 112 and 122, respectively, which cooperate to engage the tissue during sealing and cutting. It is envisioned that the electrically conductive tissue sealing surfaces 112, 122 are disposed in an angular relationship relative to one another, and may be constructed of an expandable material. In embodiments, the expandable material is a shaped memory alloy (SMA). At least one of the jaw members, e.g., jaw member 120, includes a electrically energizable cutting element 127 disposed therein, which is explained in detail below. Together, and as shown in the various figure drawings described hereafter, the electrode assembly 105 includes the combination of the sealing electrodes 112 and 122 and the cutting element(s) 127.

The various electrical connections of the electrode assembly 105 are configured to provide electrical continuity to the tissue contacting surfaces 110 and 120 and the cutting element(s) 127 through the electrode assembly 105. For example, cable lead 210 may be configured to include three different leads, namely, leads 207, 208 and 209, which carry different electrical potentials. The cable leads 207, 208 and 209 are fed through shaft 112b and connect to various electrical connectors (not shown) disposed within the proximal end of the jaw member 110, which ultimately connect to the electrically conductive sealing surfaces 112 and 122 and cutting element(s) 127. As can be appreciated, the electrical connections may be permanently soldered to the shaft 112b during the assembly process of a disposable instrument or, alternatively, selectively removable for use with a reposable instrument. Commonly owned U.S. patent application Ser. Nos. 10/474,170, 10/116,824 and 10/284,562 all disclose various types of electrical connections that may be made to the jaw members 110 and 120 through the shaft 112b the contents of all of which being incorporated by reference herein. In addition and with respect to the types of electrical connections which may be made to the jaw members 110 and 120 for endoscopic purposes, commonly-owned U.S. patent application Ser. Nos. 10/472,295, 10/116,944, 10/179,863 and 10/369,894 all disclose other types of electrical connections which are hereby incorporated by reference herein in their entirety.

The various electrical connections from lead 210 are typically dielectrically insulated from one another to allow selective and independent activation of either the tissue contacting surfaces 112 and 122 or the cutting element 127 as explained in more detail below. Alternatively, the electrode assembly 105 may include a single connector that includes an internal switch (not shown) to allow selective and independent activation of the tissue contacting surfaces 112, 122 and the cutting element 127. The leads 207, 208 and 209 (and/or conductive pathways) do not encumber the movement of the jaw members 110 and 120 relative to one another during the manipulation and grasping of tissue. Likewise, the movement of the jaw members 110 and 120 do not unnecessarily strain the lead connections.

Figure 3A:
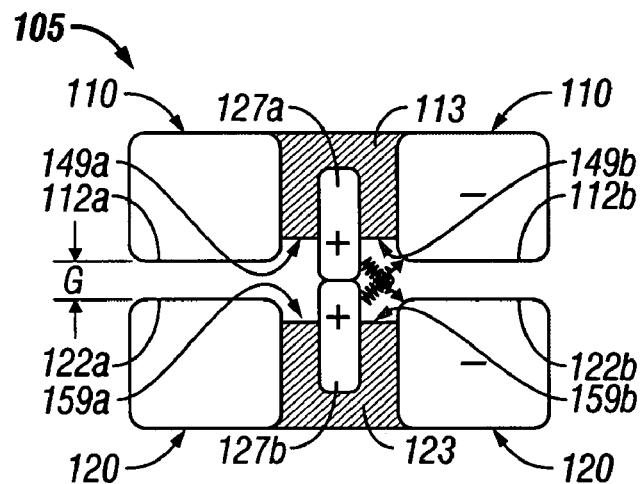
FIGS. 3A-3F are enlarged, schematic end views showing a variety of different electrode assemblies according to the present disclosure with electrical potentials identified for electrical cutting.
Figure 3B:
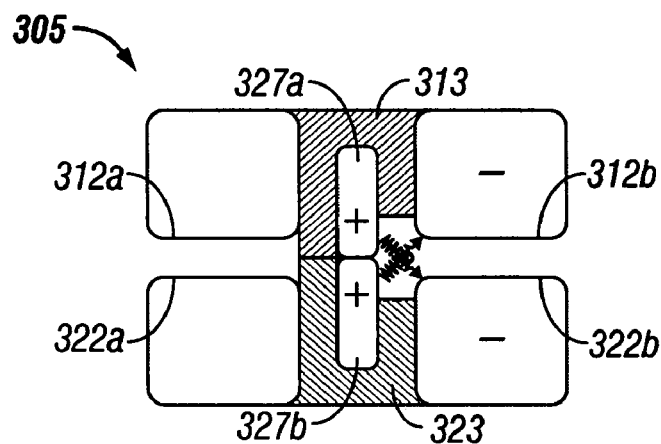
Figure 3C:
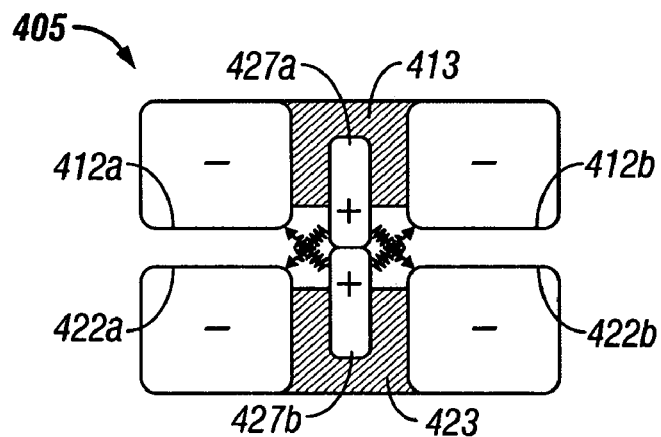
Figure 3D:
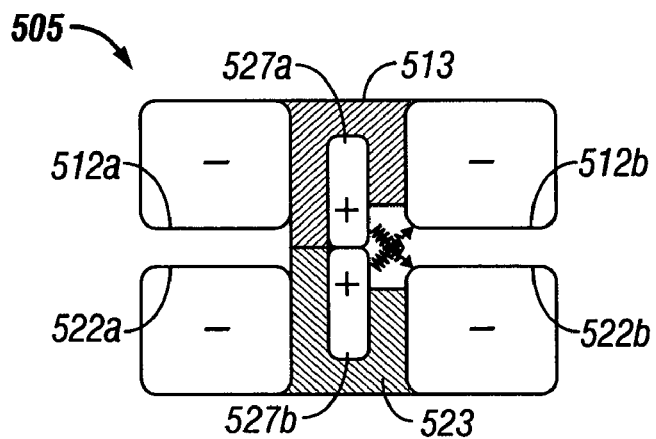
Figure 3E:
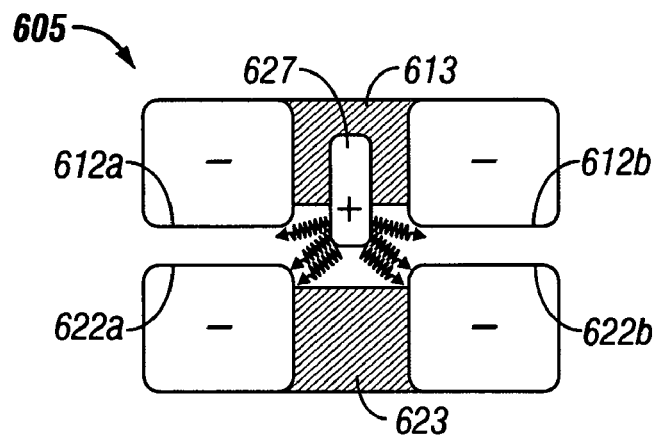
Figure 3F:
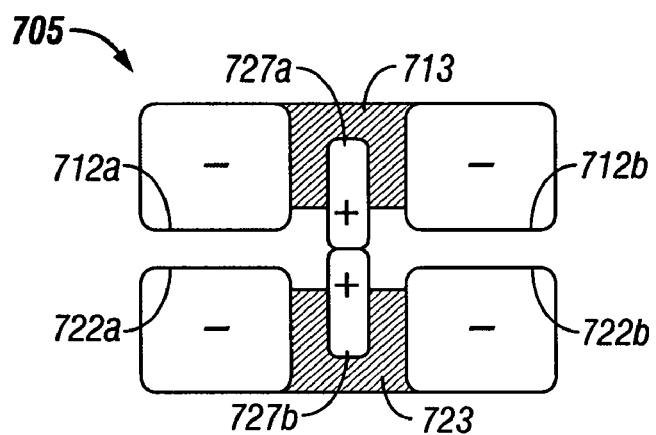

As best seen in FIGS. 2-3F, various electrical configurations of the electrode assembly 105 are shown that are designed to effectively seal and cut tissue disposed between the sealing surfaces 112 and 122 and the cutting elements 127 of the opposing jaw members 110 and 120, respectively. More particularly, and with respect to FIGS. 2 and 3A, jaw members 110 and 120 include conductive tissue contacting surfaces 112 and 122, respectively, disposed along substantially the entire longitudinal length thereof (e.g., extending substantially from the proximal to distal end of the respective jaw member 110 and 120). Tissue contacting surfaces 112 and 122 may be attached to the jaw member 110, 120 by stamping, by overmolding, by casting, by overmolding a casting, by coating a casting, by overmolding a stamped electrically conductive sealing plate and/or by overmolding a metal injection molded seal plate or in other suitable ways. All of these manufacturing techniques may be employed to produce jaw member 110 and 120 having an electrically conductive tissue contacting surface 112 and 122 disposed thereon for contacting and treating tissue.

With respect to FIG. 3A, the jaw members 110 and 120 both include an insulator or insulative material 113 and 123, respectively, disposed between each pair of electrically conductive sealing surfaces on each jaw member 110 and 120, i.e., between pairs 112a and 112b and between pairs 122a and 122b. Each insulator 113 and 123 is generally centered between its respective tissue contacting surface 112a, 112b and 122a, 122b along substantially the entire length of the respective jaw member 110 and 120 such that the two insulators 113 and 123 generally oppose one another.

One or both of the insulators 113, 123 may be made from a ceramic material due to its hardness and inherent ability to withstand high temperature fluctuations. Alternatively, one or both of the insulators 113, 123 may be made from a material having a high Comparative Tracking Index (CTI) having a value in the range of about 300 to about 600 volts. Examples of high CTI materials include nylons and syndiotactic polystyrenes. Other suitable materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

At least one jaw member 110 and/or 120 includes an electrically conductive cutting element 127 disposed substantially within or disposed on the insulator 113, 123. As described in detail below, the cutting element 127 (in many of the embodiments described hereinafter) plays a dual role during the sealing and cutting processes, namely: 1) to provide the necessary gap distance between conductive surfaces 112a, 112b and 122a, 122b during the sealing process; and 2) to electrically energize the tissue along the previously formed tissue seal to cut the tissue along the seal. With respect to FIG. 3A, the cutting elements 127a, 127b are electrically conductive; however, one or both of the cutting elements 127a, 127b may be made from an insulative material with a conductive coating disposed thereon or one (or both) of the cutting elements may be non-conductive (see, e.g., FIG. 4A). The distance between the cutting element(s) 127a and the opposing cutting element 127b (or the opposing return electrode in some cases) may be disposed within the range of about 0.000 inches to about 0.040 inches to optimize the cutting effect.

The general characteristics of the jaw members 110 and 120 and the electrode assembly 105 will initially be described with respect to FIG. 3A while the changes to the other envisioned embodiments disclosed herein will become apparent during the description of each individual embodiment. Moreover, all of the following figures show the various electrical configurations and polarities during the cutting phase only. During the so called "sealing phase", the jaw members 110 and 120 are closed about tissue and the cutting elements 127 and 127b may form the requisite gap between the opposing sealing surfaces 112a, 122a and 112b, 122b. During activation of the sealing phase, the cutting elements 127a and 127b are not necessarily energized such that the majority of the current is concentrated between opposing sealing surfaces, 112a and 122a and 112b and 122b, to effectively seal the tissue. Stop members 1160a and 1160b may also be employed to regulate the gap distance between the sealing surfaces in lieu of the cutting elements 127a and 127b. The stop members 1160a and 1160b may be disposed on the sealing surfaces 1112a, 1122a and 1112b, 1122b (see FIG. 4E), adjacent the sealing surfaces 1112a, 1122a and 1112b, 1122b or on the insulator(s) 1113, 1123.

The cutting elements 127a and 127b are configured to extend from their respective insulators 113 and 123, respectively, and extend beyond the tissue contacting surfaces 112a, 112b and 122a and 122b such that the cutting elements 127a and 127b act as stop members (i.e., creates a gap distance "G" (See FIG. 3A) between opposing conductive sealing surfaces 112a, 122a and 112b, 122b), which as mentioned above promotes accurate, consistent and effective tissue sealing. As can be appreciated, the cutting elements 127a and 127b also prevent the opposing tissue contacting surfaces 112a, 122a and 112b, 122b from touching, which eliminates the chances of the forceps 10, 100 shorting during the sealing process.

As mentioned above, two mechanical factors play an important role in determining the resulting thickness of the sealed tissue and effectiveness of a tissue seal, i.e., the pressure applied between opposing jaw members 110 and 120 and the gap distance "G" between the opposing tissue contacting surfaces 112a, 122a and 112b, 122b during the sealing process. With particular respect to vessels, the cutting element 127 (or cutting elements 127a and 127b) extends beyond the tissue contacting surfaces 112a, 112b and/or 122a, 122b to yield a consistent and accurate gap distance "G" during sealing within the range of about 0.001 inches to about 0.006 inches and, more preferably, within the range of about 0.002 inches and about 0.003 inches. Other gap ranges may be preferable with other tissue types, such as bowel or large vascular structures. As can be appreciated, when utilizing one cutting element (as with some of the disclosed embodiments herein), e.g., 127, the cutting element 127 would be configured to extend beyond the sealing surfaces 112a, 112b and 122a, 122b to yield a gap distance within the above working range. When two opposing cutting elements are utilized, e.g., 127a and 127b, the combination of these cutting elements 127a and 127b yield a gap distance within the above working range during the sealing process.

With respect to FIG. 3A, the conductive cutting elements 127a and 127b are oriented in opposing, vertical registration within respective insulators 113 and 123 of jaw members 110 and 120. Cutting elements 127a and 127b may be substantially dull so as to not inhibit the sealing process (e.g., premature cutting) during the sealing phase of the electrosurgical activation. In other words, the surgeon is free to manipulate, grasp and clamp the tissue for sealing purposes without the cutting elements 127a and 127b mechanically cutting into the tissue. Moreover, in this instance, tissue cutting can only be achieved through either: 1) a combination of mechanically clamping the tissue between the cutting elements 127a and 127b and applying electrosurgical energy from the cutting elements 127a and 127b, through the tissue and to the return electrodes, i.e., the electrically conductive tissue contacting surfaces 112b and 122b as shown in FIG. 3A; or 2) applying electrosurgical energy from the cutting elements 127a and 127b through the tissue and to the return tissue contacting surfaces 112b and 122b.

The geometrical configuration of the cutting elements 127a and 127b may play an important role in determining the overall effectiveness of the tissue cut. For example, the power density and/or current concentration around the cutting elements 127a and 127b is based upon the particular geometrical configuration of the cutting elements 127a and 127b and the cutting elements' 127a and 127b proximity to the return electrodes, i.e., tissue contacting surfaces 112b and 122b. Certain geometries of the cutting elements 127a and 127b may create higher areas of power density than other geometries. Moreover, the spacing of the return electrodes 112b and 122b to these current concentrations affects the electrical fields through the tissue. Therefore, by configuring the cutting elements 127a and 127b and the respective insulators 113 and 123 within close proximity to one another, the electrical power density remains high, which is ideal for cutting and the instrument will not short due to accidental contact between conductive surfaces. The relative size of the cutting elements 127a and 127b and/or the size of the insulator 113 and 123 may be selectively altered depending upon a particular or desired purpose to produce a particular surgical effect.

In addition, the cutting element 127a (and/or 127b) may be independently activated by the surgeon or automatically activated by the Generator once sealing is complete. A safety algorithm may be employed to assure that an accurate and complete tissue seal is formed before cutting. An audible or visual indicator (not shown) may be employed to assure the surgeon that an accurate seal has been formed and the surgeon may be required to activate a trigger (or deactivate a safety) before cutting. For example, a smart sensor or feedback algorithm may be employed to determine seal quality prior to cutting. The smart sensor or feedback loop may also be configured to automatically switch electrosurgical energy to the cutting element 127a (and/or 127b) once the smart sensor determines that the tissue is properly sealed. The electrical configuration of the electrically conductive sealing surfaces 112a, 112b and 122a, 122b may also be automatically or manually altered during the sealing and cutting processes to effect accurate and consistent tissue sealing and cutting.

Turning now to the embodiments of the electrode assembly 105, as disclosed herein, which show the various polarities during the tissue cutting phase, FIG. 3A as mentioned above includes first and second jaw members 110 and 120 having an electrode assembly 105 disposed thereon. More particularly, the electrode assembly 105 includes first electrically conductive sealing surfaces 112a and 112b each disposed in opposing registration with second electrically conductive sealing surfaces 122a and 122b on jaw members 110 and 120, respectively. Insulator 113 electrically isolates sealing surfaces 112a and 112b from one another allowing selective independent activation of the sealing surfaces 112a and 112b. Insulator 123 separates sealing surfaces 122a and 122b from one another in a similar manner thereby allowing selective activation of sealing surfaces 122a and 122b.

Each insulator 113 and 123 is set back a predetermined distance between the sealing surfaces 112a, 112b and 122a, 122b to define a recess 149a, 149b and 159a, 159b, respectively, which, as mentioned above, affects the overall power densities between the electrically activated surfaces during both the sealing and cutting phases. Cutting element 127a is disposed within and/or deposited on insulator 113 and extends inwardly therefrom to extend beyond the sealing surfaces 112a, 112b by a predetermined distance. In the embodiments wherein only one cutting element, e.g., 127a, is shown, the cutting element 127a extends beyond the sealing surfaces 112a, 112b and 122a and 122b to define the aforementioned gap range between the opposing sealing surfaces 112a, 122a and 112b and 122b. When two (or more) cutting elements 127a and 127b are employed (e.g., at least one disposed within each insulator 113 and 123) the combination of the cutting elements 127a and 127b yield the desired gap distance within the working gap range.

During sealing, the opposing sealing surfaces 112a, 122a and 112b, 122b are activated to seal the tissue disposed therebetween to create two tissue seals on either side of the insulators 113 and 123. During the cutting phase, the cutting elements 127a and 127b are energized with a first electrical potential "+" and the right opposing sealing surfaces 112b and 122b are energized with a second electrical potential "−". This creates a concentrated electrical path between the potentials "+" and "−" through the tissue to cut the tissue between the previously formed tissue seals. Once the tissue is cut, the jaw members 110 and 120 are opened to release the two tissue halves.

FIG. 3B discloses another embodiment according to the present disclosure that includes similar elements as described above with respect to FIG. 3A, namely, sealing surfaces 312a, 312b and 322a, 322b, insulators 313 and 323 and cutting elements 327a and 327b with the exception that the left side of each insulator 313 and 323 is extended beyond sealing surfaces 312a and 322a to a position that is flush with the cutting elements 327a and 327b. The right side of each insulator 313 and 323 is set back from sealing surfaces 312a and 312b, respectively. Configuring the electrode assembly 305 in this fashion may reduce stray current concentrations between electrically conductive surfaces 312a, 312b and 322a, 322b and cutting elements 327a and 327b especially during the cutting phase.

FIG. 3C discloses yet another embodiment according to the present disclosure and includes similar elements as above, namely, sealing surfaces 412a, 412b and 422a, 422b, insulators 413 and 423 and cutting elements 327a and 327b. With this particular embodiment, during the cutting phase, both sets of opposing sealing surfaces 412a, 422a and 412b, 422b are energized with the second electrical potential "−" and the cutting elements 427a and 427b are energized to the first electrical potential "+". It is believed that this electrode assembly 405 may create concentrated electrical paths between the potentials "+" and "−" through the tissue to cut the tissue between the previously formed tissue seals.

FIG. 3D shows an electrode assembly 505 configuration similar to FIG. 3B with a similar electrical configuration to the embodiment of FIG. 3C. The electrode assembly 505 includes and includes similar components as described above, namely, sealing surfaces 512*a*, 512*b* and 522*a*, 522*b*, insulators 513 and 523 and cutting elements 527*a* and 527*b*. The opposing sealing electrodes 512*a*, 522*b* and 512*a*, 522*b* are energized to the second electrical potential "−" during the cutting phase, which as described above is believed to enhance tissue cutting. With particular embodiments like FIGS. 3C and 3D, it may be easier to manufacture the electrode assembly 505 such that all of the sealing surfaces 512*a*, 512*b* and 522*a*, 522*b* are energized to the same electrical potential rather than employ complicated switching algorithms and/or circuitry to energize only select sealing surfaces like FIGS. 3A and 3B.

FIG. 3E shows yet another embodiment of the electrode assembly 605 that includes opposing sealing surfaces 612*a*, 622*a* and 612*b*, 622*b*, cutting element 627 and insulators 613 and 623. By this particular embodiment, the electrode assembly 605 only includes one cutting element 627 disposed within insulator 613 for cutting tissue. The cutting element 627 is disposed opposite insulator 623, which provides a dual function during activation of the electrode assembly 605: 1) provides a uniform gap between sealing surfaces 612*a*, 622*a* and 612*b*, 622*b* during the sealing phase; and 2) prevents the electrode assembly 605 from shorting during the sealing and cutting phases. During activation, the cutting element 627 is energized to a first potential "+" and the opposing sealing surfaces 612*a*, 622*a* and 612*b*, 622*b* are energized to a second electrical potential which creates an area of high power density between the two previously formed tissue seals and cuts the tissue.

FIG. 3F shows yet another alternate embodiment of the electrode assembly 705 that includes similar elements as described above, namely, sealing surfaces 712*a*, 712*b* and 722*a*, 722*b*, cutting elements 727*a* and 727*b* and insulators 713 and 723. During activation, only three of the four sealing surfaces are energized to the second potential "−", e.g., sealing surfaces 712*a*, 712*b* and 722*b* while the cutting elements 727*a* and 727*b* are energized to the first potential "+".

Figure 4A:
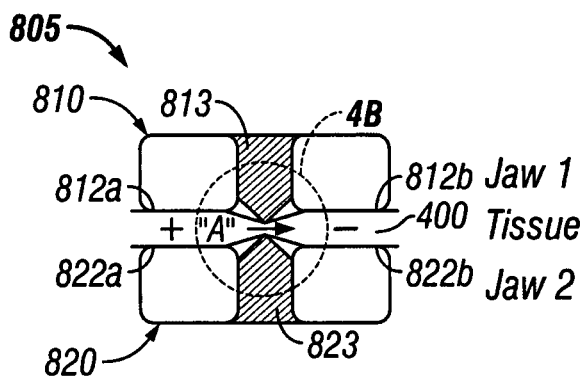
FIG. 4A is an enlarged, schematic end view showing one electrode assembly configuration with tissue disposed between the jaw members.
Figure 4B:
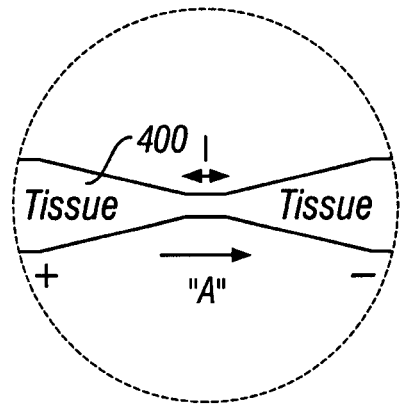
FIG. 4B is a schematic end view showing the area of detail of FIG. 4A.

FIGS. 4A and 4B shows yet another embodiment of the electrode assembly 805 according to the present disclosure showing tissue disposed between the two jaw members 810 and 820 prior to activation of the sealing surfaces 812*a*, 812*b* and 822*a*, 822*b*. With this particular embodiment, the insulators 813 and 823 are configured to have opposing triangular like cross sections, which essentially "pinch" the tissue between the insulators 813 and 823 when tissue is grasped between jaw members 810 and 820. During sealing, energy is applied to the tissue through the opposing sealing plates 812*a*, 822*a* and 812*b*, 822*b* to effect two tissue seals on either side of the insulators 813 and 823. During the cutting phase, sealing electrodes 812*a* and 822*a* are energized to a first potential "+" and sealing plates 812*b* and 822*b* are energized to the second electrical potential "−" such that energy flows in the direction of the indicated arrow "A". In other words, it is believed that the pinching of the tissue tends to control or direct the energy concentration to specific tissue areas to effect tissue cutting.

Turning now to FIGS. 4C-4J, various geometrical configurations for the upper jaw member 910 for the electrode assembly 905 which may be utilized with a symmetrical or asymmetrical lower jaw member (not shown) to effectively seal and subsequently cut tissue. Using the various geometries of the jaw members tends to "pinch" the tissue during sealing prior to separation, which may enhance the tissue cutting process especially when the pinched tissue areas are subject to high power densities. For the purposes herein, the pinch may be described as the area of smallest tissue volume anywhere between the active tissue poles. Typically, the pinched tissue area is associated with high pressure. Many of the below described jaw configurations illustrate the pinch concept and are envisioned to utilize a variety of polarity configurations to enhance or facilitate cutting. For the purposes of clarification, only the polarity associated with the cutting phase is depicted on each figure.

Moreover, any combination of electrical potential as hereinbefore described may be utilized with the various jaw members (and each jaw member's opposing jaw member) to effectively seal tissue during a first electrical phase and cut tissue during a subsequent electrical phase. As such, the illustrated jaw members are labeled with a first electrical potential "+"; however, the lower jaw member inclusive of the sealing surfaces and cutting elements (which may or may not be a mirror image of the upper jaw member) may be energized with any combination of first and second electrical potential(s) (or other electrical potentials) to effectively seal and subsequently cut tissue disposed between the jaw members.

Figure 4C:
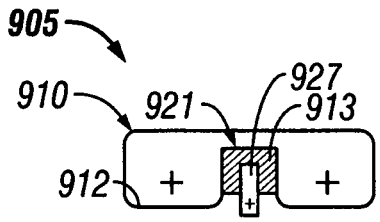
FIGS. 4C-4J are enlarged, schematic end views showing various configurations for an upper jaw member to promote electrical cutting.
Figure 4D:
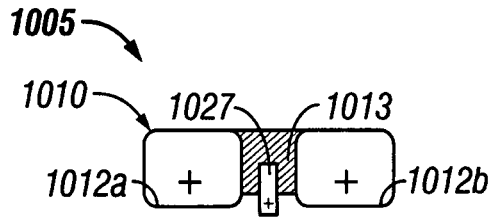

FIG. 4C shows one particular upper jaw member 910 that includes a sealing surface 912 having a U-shaped recess 921 defined therein for housing insulator 913. A cutting element 927 is disposed within insulator 913 and is dimensioned to extend beyond the sealing surface 912. The cutting element 927 may be an electrode or may be made from a partially conductive material. FIG. 4D shows a jaw member 1010 that forms part of an electrode assembly 1005 that includes two sealing surfaces 1012*a* and 1012*b* with an insulator 1013 disposed therebetween. The insulator 1013 includes a cutting element 1027 disposed therein that extends beyond the sealing surfaces 1012*a* and 1012*b* much like the embodiments described above with respect to FIGS. 3A-3F. Again, the cutting element 1027 may be an electrode or made from a semi-conductor material. However, and as mentioned above, a different geometrically-shaped jaw member may be disposed opposite jaw member 1010 with different electrical potentials to produce a particular sealing and cutting effect.

FIGS. 4E-4J show various geometrical configurations of at least one jaw member that is configured to both seal tissue during a first sealing phase and cut tissue during a subsequent cutting phase. In each instance, the particular geometrical configuration of the insulator is designed to focus current into high areas of power density to produce a cutting effect and/or reduce the likelihood of current straying to adjacent tissue, which may ultimately damage the adjacent tissue structures.

Figure 4E:
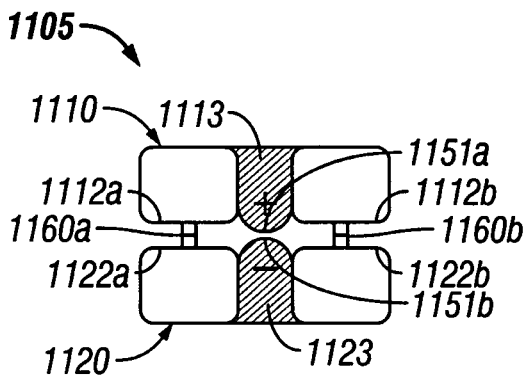

For example, FIG. 4E shows a jaw member 1110 that may be utilized with the electrode assembly 1105 which includes sealing surfaces 1112*a* and 1112*b* that are separated by a partially conductive material 1113. A mirror-like jaw member 1120 is shown in opposition to jaw member 1110 and includes similar elements, namely, sealing surfaces 1122*a* and 1122*b* and partially conductive material 1123. In this particular embodiment, the partially conductive materials 1113 and 1123 are generally rounded to include and apexes 1151*a* and 1151*b*, respectively, which extend beyond the sealing surfaces 1112*a*, 1112*b* and 1122*a*, 1122*b*. The partially conductive materials 1113 and 1123 are typically made from a material that have conductive properties that over time generate areas of high power density at the apexes 1151*a* and 1151*b* to cut tissue disposed thereunder. A series of stop members 1160a and 1160 may be disposed on surfaces 1112a and 1122b and prevent the apexes 1151a and 1151b from touching and shorting.

During the sealing phase (not shown) the partially conductive materials 1113 and 1123 are not energized and will generally act more as insulating materials since by its nature it is only semi-conductive and are not as conductive as sealing surfaces 1112a, 1112b and 1122a, 1122b. In other words, the current may be supplied to the sealing plates 1112a, 1112b and 1122a, 1122b and not directly to the partially conductive materials 1113 and 1123, thereby producing the majority of the electrical effect between the opposing sealing plates 1112a, 1122a and 1112b, 1122b of the jaw members 1110 and 1120. During the cutting phase (as shown), an electrical potential is supplied directly to the partially conductive materials 1113 and 1123, which is believed will make them more conductive and which produce areas of high power density in the vicinity of the apexes 1151a and 1151b to cut the tissue.

For example, partially conductive material 1113 is supplied with a first potential and partially conductive material 1123 is supplied with a second potential to facilitate cutting. Jaw member 1120 may also be configured to include a different geometrical configuration from jaw member 1110 to produce a particular cutting effect. Moreover, an insulator (not shown) may be disposed between one or both of the partially conductive materials 1113 and 1123 and its respective sealing surface to reduce electrical conduction or heat transfer between or across these elements.

Figure 4F:
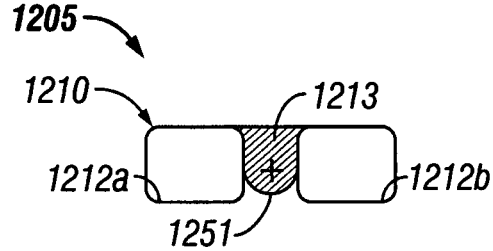

FIG. 4F shows a similar electrode assembly 1205 having sealing surfaces 1212a and 1212b that are separated by a partially conductive material 1213 and wherein the partially conductive material 1213 is generally rounded but does not extend beyond the sealing surfaces 1212a and 1212b. The partially conductive material 1213 may be made from a material such as those identified above that produces an area of high power density at the apex 1251 to cut tissue disposed thereunder during the cutting phase. Again, the opposite jaw member (not shown) may be configured as a mirror image of the jaw member 1210 or may include a different geometrical configuration.

Figure 4G:
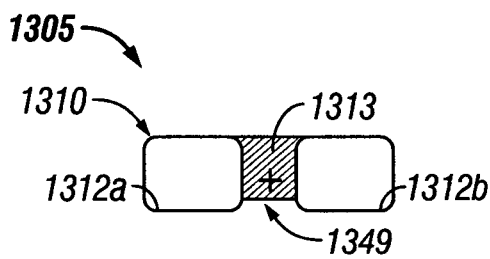
Figure 4H:
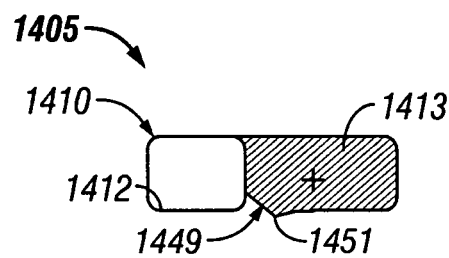

FIG. 4G shows another geometric configuration of a jaw member 1310 that includes sealing surfaces 1312a and 1312b separated by a partially conductive material 1313 wherein the partially conductive material is set back between the sealing surface 1312a and 1312b to define a recess 1349 therein. FIG. 4H shows yet another geometric configuration of a jaw member 1410 which forms part of an electrode assembly 1405 and that includes sealing surface 1412 and a partially conductive material 1413. As can be appreciated this particular arrangement does not include a second sealing surface on the upper jaw member 1410 but instead the partially conductive material 1413 includes a notch-like recess 1449 defined therein that has a cutting tip 1451, which extends beyond sealing surface 1412. The cutting tip 1451 extends beyond the sealing surface 1412 enough to both maintain the necessary gap distance during the sealing phase and to eventually facilitate tissue cutting during the cutting phase by producing an area of high power density at the tip 1451. Again, the opposite jaw member (not shown) may be configured as a mirror image of the jaw member 1410 or may include a different geometrical configuration.

Figure 4I:
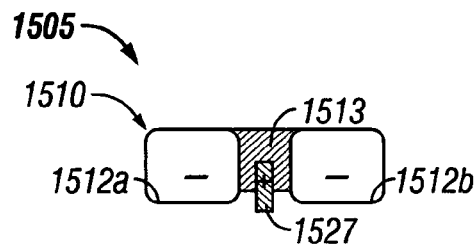

FIG. 4I includes yet another geometric configuration of the upper jaw member 1510 that forms part of an electrode assembly 1505 and that includes sealing surfaces 1512a and 1512b that are separated by an insulator 1513. The insulator 1513 includes a generally rectilinear-shaped semi-conductive cutting element 1527 disposed therein, which extends beyond the sealing surfaces 1512a and 1512b. During the cutting phase, the semi-conductive cutting element 1527 is energized by a first potential "+" and the sealing plates 1512a, 1512b is energized to a second potential "−". The insulator 1513 isolates the potentials between the partially conductive material 1527 and the sealing surfaces 1512a and 1512b during activation.

Figure 4J:
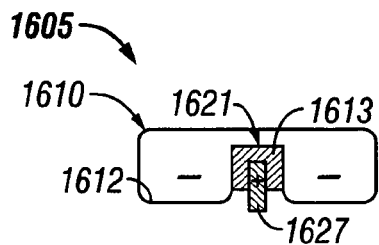

FIG. 4J shows still yet another geometric configuration showing a jaw member 1610 for an electrode assembly 1605 that is similar to FIG. 4C above and includes a C-shaped sealing plate 1612 having a recess 1621 defined therein for housing an insulator 1613. The insulator 1613 includes a semi-conductive cutting element 1627 housed therein for cutting tissue. During the cutting phase, the semi-conductive cutting element 1627 is energized to a first potential "+" and the sealing plate 1612 is energized to a second potential "−" to effect tissue cutting. Again, the lower or second jaw member (not shown) may include the same geometric configuration to enhance the cutting process.

Figure 5:
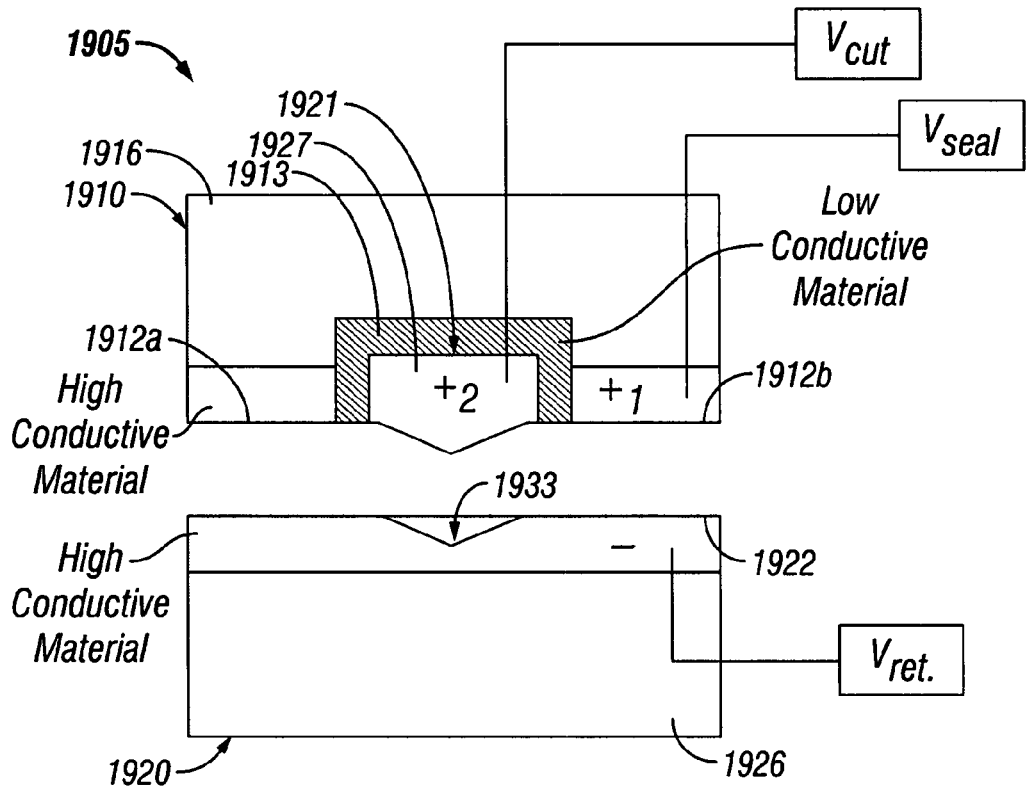
FIG. 5 is a schematic end view showing an alternate configuration of an electrode assembly according to the present disclosure with the electrical potentials for both the sealing phase and the cutting phase identified.

FIG. 5 shows a schematically-illustrated example of electrical circuitry for an electrode assembly 1905, which may be utilized to initially seal tissue between the sealing plates and subsequently cut tissue once the tissue seal(s) are formed. More particularly, jaw member 1910 includes insulative housing 1916 that is dimensioned to house conductive sealing plates 1912a and 1912b with an insulator or partially conductive material 1913 disposed therebetween. Insulator/partially conductive material 1913 includes a recess 1921 defined therein that is dimensioned to retain a generally triangularly-shaped cutting element 1927 and extends beyond sealing surfaces 1912a and 1912b. Jaw member 1920 includes an outer insulative housing 1926 that is dimensioned to house electrically conductive sealing surface 1922. Sealing surface 1922 includes a recess 1933 defined therein that generally compliments the cross sectional profile of cutting element 1927. The cutting element 1927 is dimensioned slightly larger than the recess 1933 such that a gap is formed when the jaw members are closed about tissue, the gap being within the above-identified working range.

During sealing (Vseal), the sealing plates 1912a and 1912b are energized to a first potential "$+_1$" and sealing plate 1922 is energized to a second potential "−". The cutting element is not energized. Since the insulator or semi-conductor does not conduct energy as well as the conductive sealing plates 1912a and 1912b, the first potential is not effectively or efficiently transferred to the cutting element 1927 and the tissue is not necessarily heated or damaged during the sealing phase. During the sealing phase energy is transferred from the sealing plates 1912a and 1912b through the tissue and to the return electrode 1922 (Vreturn). It is believed that even if some energy is effectively transferred to the cutting element 1927 during the sealing phase, it will simply preheat or pre-treat the tissue prior to separation and should not affect the cutting phase. During the sealing phase, the cutting element 1927 mainly acts as a stop member for creating and maintaining a gap between the opposing sealing surfaces 1912a, 1912b and 1922.

During the cutting phase (Vcut), a first potential "$+_2$" is supplied to the cutting element 1927 and a second potential "−" is supplied to the sealing surface 1922. The electrical parameters (power, current, waveform, etc.) associated with this phase may be the same or different than the potentials used for the sealing phase. It is believed that similar first and second potentials may be utilized since different components with varying geometries are being energized, which by themselves may create different electrical effects. As can be appreciated, during the cutting phase energy is transferred from the cutting element 1927 through the tissue and to the return electrode 1922 (Vreturn). It is believed that even if some energy is transferred to the sealing plates 1912a and 1912b during the cutting phase through the insulator/semi-conductor 1913, it will not detrimentally effect the already formed tissue seals. Moreover, it is believed that one or more sensors (not shown), computer algorithms and/or feedback controls associated with the generator or internally disposed within the forceps may be employed to prevent overheating of the tissue during the sealing and cutting phases.

Figure 6A:
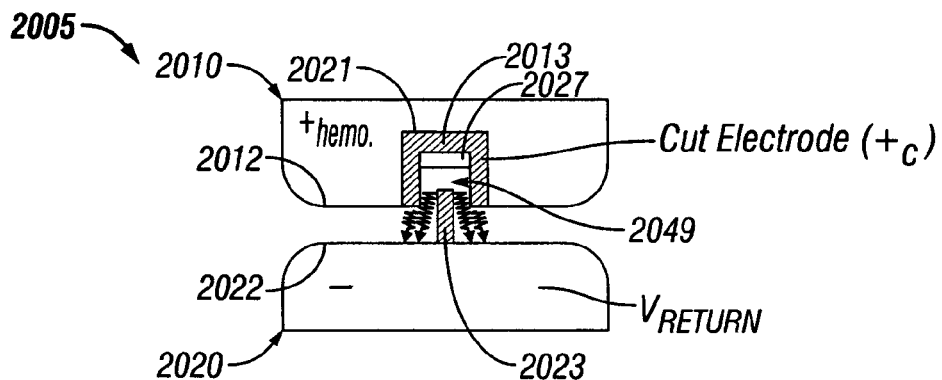
FIGS. 6A-6D are enlarged, schematic end views showing alternate configurations of the electrode assembly according to the present disclosure with the electrical potentials for both the sealing mode and the cutting mode identified.

FIGS. 6A-6D show additional embodiments of jaw members having various electrode assemblies that may be utilized for sealing and cutting tissue disposed between the jaw members. For example, FIG. 6A shows a first or upper jaw member 2010 for use with an electrode assembly 2005 that includes an electrically conductive sealing surface 2012 having a recess 2021 defined therein dimensioned to house an insulator 2013. The insulator also includes a notch 2049 disposed therein that partially houses a generally rectilinearly-shaped cutting electrode 2027. Electrode 2027 is recessed or set back within notch 2049. Jaw member 2020 includes an electrically conductive sealing surface 2022 that is disposed in substantial vertical registration with opposing sealing surface 2012. Sealing surface 2022 includes a generally rectilinearly-shaped insulator 2023 that extends towards jaw member 2010 and is configured to abut electrode 2027 when the jaw members 2010 and 2020 are moved into the closed position about tissue. As can be appreciated, the insulator 2023 acts as a stop member and creates a gap distance within the above working range during the sealing process. In addition, the two insulators 2013 and 2023 insulate the upper jaw member 2010 during the cutting phase and generally direct the cutting current from the cutting element 2027 in an intense fashion towards the return electrode 2022 (Vreturn) to effectively cut tissue.

Figure 6B:
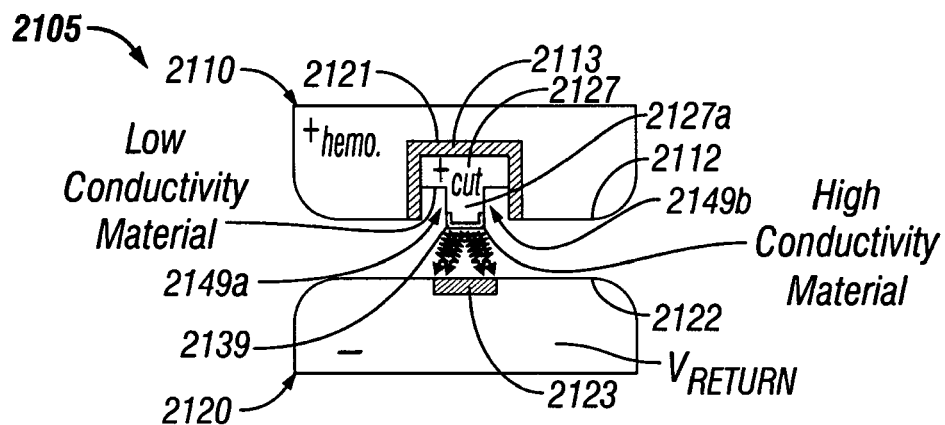

FIG. 6B shows yet another embodiment of an electrode assembly 2105 disposed on jaw members 2110 and 2120. More particularly, jaw members 2110 and 2120 include electrically conductive sealing surfaces 2112 and 2122, respectively, disposed in general vertical registration relative to one another and that are configured to seal tissue during the sealing phase. Much like the embodiment described above with respect to FIG. 6A, jaw member 2110 includes a recess 2121 defined therein dimensioned to house an insulator 2113. Jaw member 2120 includes an electrically conductive sealing surface 2122 that is disposed in substantial vertical registration with opposing sealing surface 2112. Jaw member 2120 includes an insulator 2123 disposed therein that is disposed opposite recess 2121.

The insulator 2113 also includes a T-shaped cutting element 2127 housed therein which defines two notches 2149a and 2149b on either side of a leg or extension 2127a which extends towards jaw member 2120. The cutting element 2127 may be made from a relatively low conductive material and includes an area of highly conductive material 2139 disposed at the distal end of the leg 2127a. The highly conductive material 2139 is disposed in vertical registration with the insulator 2123 disposed in jaw member 2120. During activation of the cutting phase, it is believed that the highly conductive material 2139 will focus the cutting current in an intense fashion towards the return electrode 2122 (Vreturn) to cut the tissue disposed between jaw members 2110 and 2120.

Figure 6C:
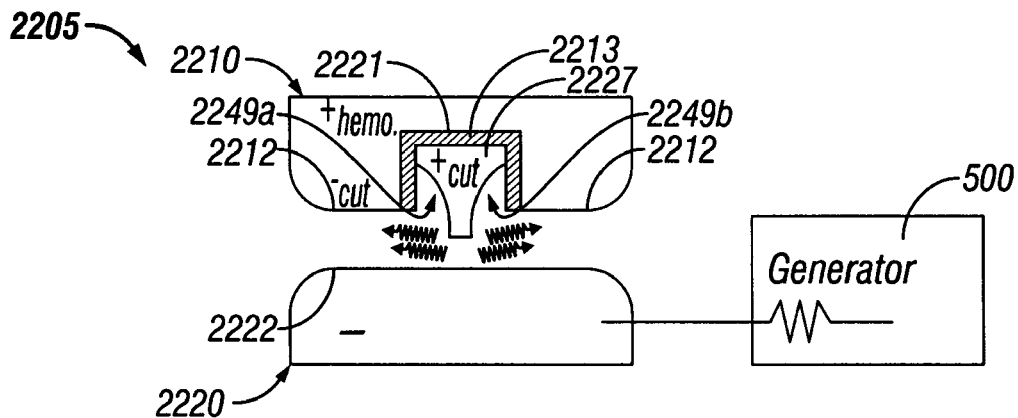

FIG. 6C shows yet another set of jaw members 2210 and 2220 with an electrode assembly 2205 disposed thereon for sealing and cutting tissue. More particularly, jaw member 2210 includes an electrically conductive sealing surface 2212 having a recessed portion 2221 disposed therein for housing an insulator 2213 which, in turn, houses a generally V-shaped cutting element 2227 therein. Jaw member 2220 includes an electrically conductive sealing surface 2222 which opposes sealing surface 2212 on jaw member 2210. During the sealing phase, sealing surfaces 2212 and 2222 conduct electrosurgical energy through tissue held therebetween to effect a tissue seal. V-shaped cutting element 2227 acts as a stop member during the sealing phase.

During the cutting phase, V-shaped cutting element 2227 pinches the tissue held between the jaw members 2210 and 2220 and when activated directs electrosurgical energy through the tissue in an intense fashion around insulator 2213 and towards sealing surface 2212. Jaw member 2220 remains neutral during the cutting phase and is not believed to significantly alter the direction of the electrical path to adversely effect the cutting process.

Figure 6D:
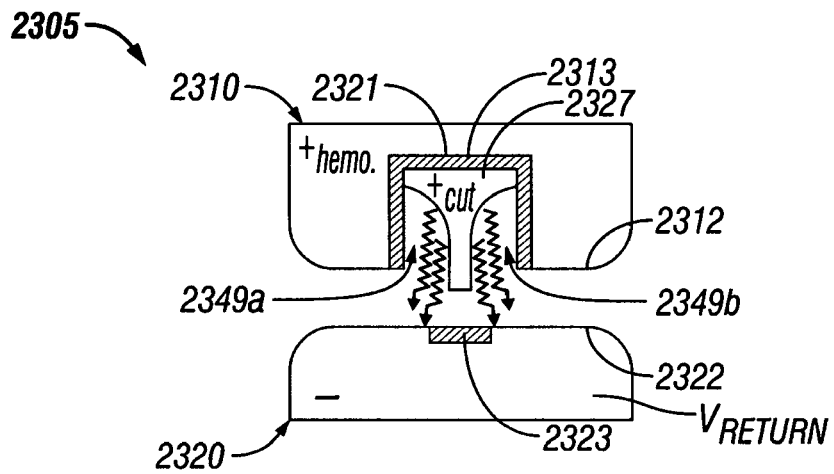

FIG. 6D shows yet another embodiment of jaw members 2310 and 2320 having an alternative electrode assembly 2305 for sealing and cutting tissue. More particularly, the electrode assembly 2305 is similar to the electrode configuration of the embodiment described with respect to FIG. 6C with the exception that the lower jaw member 2320 includes an insulator 2323 disposed in vertical registration with the cutting element 2327 disposed within the recess 2321 of the upper jaw member 2310. In this instance, the cutting element 2327 is dimensioned to be wider than the insulator 2323 such that the rear portions of the V-shaped cutting element extend laterally beyond the insulator 2323 when the jaw members 2310 and 2320 are disposed in the closed position. In other words, the cutting element 2327 includes an overhang portion which is disposed in opposing vertical registration with the return electrode 2322. The insulator 2313 disposed within the recess 2321 of the upper jaw member 2310 helps to direct the electrosurgical energy towards the return electrode 2322 during cutting and reduces stray currents to adjacent tissue structures.

During the sealing phase, sealing surfaces 2312 and 2322 conduct electrosurgical energy through tissue held therebetween to effect two tissues seals on opposite sides of insulator 2313. V-shaped cutting element 2327 acts as a stop member during the sealing phase. During the cutting phase, jaw member 2310 is neutralized and cutting element 2327 is energized such that electrosurgical energy is directed from the cutting element 2327 through tissue held between the jaw members 2310 and 2320 and to the return electrode 2322 (Vreturn). It is believed that the V-shaped cutting element 2327 will direct energy to the return electrode 2322 in an intense fashion around insulator 2323 and towards sealing surface 2212 to effectively cut the tissue between the already formed tissue seals.

Figure 7A:
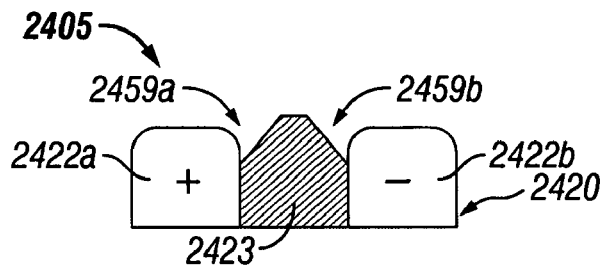
FIGS. 7A-7E are enlarged, schematic end views showing various configurations for the lower jaw member to promote electrical cutting.

FIGS. 7A-7D show various geometric configurations of cutting elements and insulators for use with the electrode assemblies of forceps 10, 100 according to the present disclosure. For example, FIG. 7A shows one embodiment wherein one of the electrode assemblies 2405 includes jaw members 2420 having first and second electrically conductive sealing surfaces 2422a and 2422b which are of opposite electrical potentials and which are separated by a trapeziodally-shaped insulator 2423 which extends beyond each respective sealing surface 2422a and 2422b. As can be appreciated the particular shape of the frustoconically-shaped insulator 2423 forms two recessed portions 2459a and 2459b between the sealing surfaces 2422a, 2422b and the insulator 2423 which is envisioned to both pinch the tissue between the insulator 2423 and the opposing surface (e.g., another insulator or conductive surface) and control the electrosurgical energy during activation to facilitate cutting.

Figure 7B:
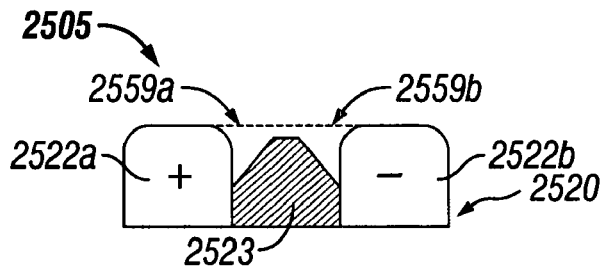

FIG. 7B shows another similar embodiment which includes a frustoconically-shaped insulator 2523 which does not extend beyond the sealing surfaces 2522a and 2522b but is actually slightly set back from the sealing surfaces 2522a and 2522b. Again, the particular shape of the trapezoidally-shaped insulator 2523 forms two recessed portions 2559a and 2559b between the sealing surfaces 2522a, 2522b and the insulator 2523 which is envisioned to control the electrosurgical energy during activation to enhance the cutting process.

Figure 7C:
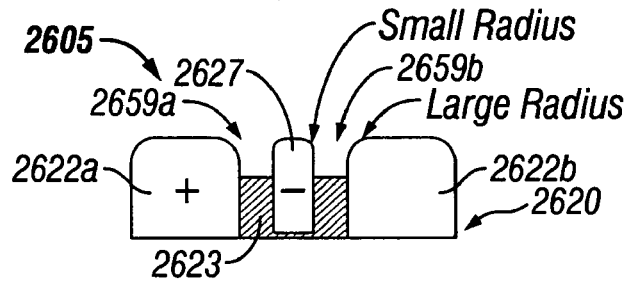

FIG. 7C shows another geometrical configuration of an electrode assembly 2605 which includes one active electrically conductive surface 2622a and one neutral electrically conductive surface 2622b during the cutting phase. A cutting element 2627 is disposed between the two surfaces 2622a and 2622b and is separated from the surfaces by an insulator 2623 which is recessed between the two surfaces 2622a and 2622b to form notches or set back areas 2659a and 2659b. The cutting element 2627 is designed with a smaller radius of curvature than the active electrode 2622a such that during the cutting phase, electrosurgical energy is intensified to create a sufficient power density to effectively cut tissue proximate the cutting element 2627.

Figure 7D:
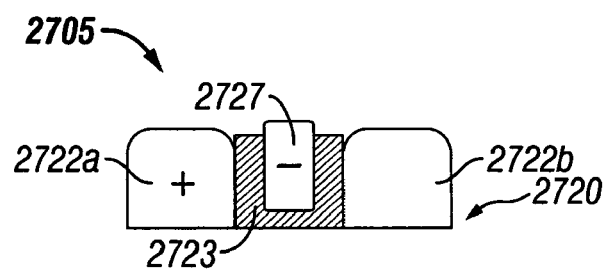

FIG. 7D shows another geometric configuration of an electrode assembly 2705 similar to the embodiment shown in FIG. 7C above wherein the insulator 2723 is configured to be generally flush with the surfaces 2722a and 2722b. The cutting element 2727 is disposed within the insulator 2723 and extends from both the insulator 2723 and the surfaces 2722a and 2722b towards an opposing surface on the other jaw member (not shown). It is believed that the shape of the insulator 2723 will direct intensified electrosurgical current between the cutting element 2727 and the active conductive surface 2722a.

Figure 7E:
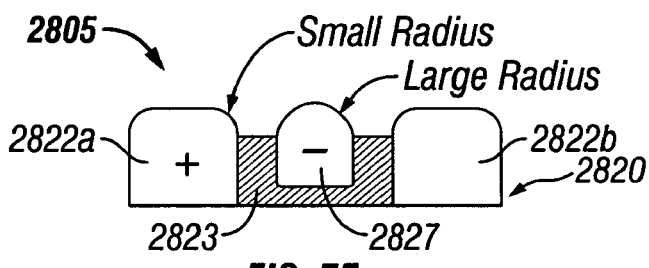

FIG. 7E shows yet another electrode assembly 2805 having a jaw member 2820 with a geometric configuration similar FIG. 7C above wherein the insulator 2823 is recessed between the two sealing surfaces 2822a and 2822b. A generally rounded cutting element 2827 is disposed within the insulator 2823. The cutting element 2827 includes a larger radius of curvature than the radius of curvature of the active surface 2822a such that during the cutting phase, electrosurgical energy is intensified to effectively cut tissue proximate the cutting element 2827.

As can be appreciated, the various geometrical configurations and electrical arrangements of the electrode assemblies allow the surgeon to initially activate the two opposing electrically conductive tissue contacting surfaces and seal the tissue and, subsequently, selectively and independently activate the cutting element and one or more tissue contacting surfaces to cut the tissue utilizing the various shown electrode assembly configurations. Hence, the tissue is initially sealed and thereafter cut without re-grasping the tissue.

However, the cutting element and one or more tissue contacting surfaces may also be activated to simply cut tissue/vessels without initially sealing. For example, the jaw members may be positioned about tissue and the cutting element may be selectively activated to separate or simply coagulate tissue. This type of alternative embodiment may be particularly useful during certain endoscopic procedures wherein an electrosurgical pencil is typically introduced to coagulate and/or dissect tissue during the operating procedure.

A switch 70 may be employed to allow the surgeon to selectively activate one or more tissue contacting surfaces or the cutting element independently of one another. As can be appreciated, this allows the surgeon to initially seal tissue and then activate the cutting element by simply turning the switch.

Rocker switches, toggle switches, flip switches, dials, etc. are types of switches which can be commonly employed to accomplish this purpose. The switch may also cooperate with the smart sensor (or smart circuit, computer, feedback loop, etc.) which automatically triggers the switch to change between the "sealing" mode and the "cutting" mode upon the satisfaction of a particular parameter. For example, the smart sensor may include a feedback loop which indicates when a tissue seal is complete based upon one or more of the following parameters: tissue temperature, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal. A separate lead may be connected between the smart sensor and the generator for visual and/or audible feedback purposes.

The generator 500 delivers energy to the tissue in a pulse-like waveform. It has been determined that delivering the energy in pulses increases the amount of sealing energy which can be effectively delivered to the tissue and reduces unwanted tissue effects such as charring. Moreover, the feedback loop of the smart sensor can be configured to automatically measure various tissue parameters during sealing (i.e., tissue temperature, tissue impedance, current through the tissue) and automatically adjust the energy intensity and number of pulses as needed to reduce various tissue effects such as charring and thermal spread.

It has also been determined that RF pulsing may be used to more effectively cut tissue. For example, an initial pulse from the cutting element through the tissue (or the tissue contacting surfaces through the tissue) may be delivered to provide feedback to the smart sensor for selection of the ideal number of subsequent pulses and subsequent pulse intensity to effectively and consistently cut the amount or type of tissue with minimal effect on the tissue seal. If the energy is not pulsed, the tissue may not initially cut but desiccate since tissue impedance remains high during the initial stages of cutting. By providing the energy in short, high energy pulses, it has been found that the tissue is more likely to cut.

Alternatively, a switch may be configured to activate based upon a desired cutting parameter and/or after an effective seal is created or has been verified. For example, after effectively sealing the tissue, the cutting element may be automatically activated based upon a desired end tissue thickness at the seal.

As mentioned in many of the above embodiments, upon compression of the tissue, the cutting element acts as a stop member and creates a gap "G" between the opposing conductive tissue contacting surfaces. Particularly with respect to vessel sealing, the gap distance is in the range of about 0.001 to about 0.006 inches. As mentioned above, controlling both the gap distance "G" and clamping pressure between conductive surfaces are two important mechanical parameters which need to be properly controlled to assure a consistent and effective tissue seal. The surgeon activates the generator to transmit electrosurgical energy to the tissue contacting surfaces and through the tissue to affect a seal. As a result of the unique combination of the clamping pressure, gap distance "G" and electrosurgical energy, the tissue collagen melts into a fused mass with limited demarcation between opposing vessel walls.

Once sealed, the surgeon activates the cutting element to cut the tissue. As mentioned above, the surgeon does not necessarily need to re-grasp the tissue to cut, i.e., the cutting element is already positioned proximate the ideal, center cutting line of the seal. During the cutting phase, highly concentrated electrosurgical energy travels from the cutting element through the tissue to cut the tissue into two distinct halves. As mentioned above, the number of pulses required to effectively cut the tissue and the intensity of the cutting energy may be determined by measuring the seal thickness and/or tissue impedance and/or based upon an initial calibrating energy pulse which measures similar parameters. A smart sensor (not shown) or feedback loop may be employed for this purpose.

As can be appreciated, the forceps may be configured to automatically cut the tissue once sealed or the instrument may be configured to permit the surgeon to selectively divide the tissue once sealed. Moreover, it is envisioned that an audible or visual indicator (not shown) may be triggered by a sensor (not shown) to alert the surgeon when an effective seal has been created. The sensor may, for example, determine if a seal is complete by measuring one of tissue impedance, tissue opaqueness and/or tissue temperature. Commonly-owned U.S. application Ser. No. 10/427,832 which is hereby incorporated in its entirety by reference herein describes several electrical systems which may be employed to provide positive feedback to the surgeon to determine tissue parameters during and after sealing and to determine the overall effectiveness of the tissue seal.

The electrosurgical intensity from each of the electrically conductive surfaces and cutting elements may be selectively or automatically controllable to assure consistent and accurate cutting along the centerline of the tissue in view of the inherent variations in tissue type and/or tissue thickness. Moreover, it is contemplated that the entire surgical process may be automatically controlled such that after the tissue is initially grasped the surgeon may simply activate the forceps to seal and subsequently cut tissue. In this instance, the generator may be configured to communicate with one or more sensors (not shown) to provide positive feedback to the generator during both the sealing and cutting processes to insure accurate and consistent sealing and division of tissue. Any suitable feedback mechanism may be employed for this purpose.

From the foregoing and with reference to the various figure drawings, those skilled in the art will appreciate that certain modifications can also be made to the present disclosure without departing from the scope of the present disclosure. For example, cutting element may be dimensioned as a cutting wire which is selectively activatable by the surgeon to divide the tissue after sealing. More particularly, a wire is mounted within the insulator between the jaw members and is selectively energizable upon activation of the switch.

The forceps may be designed such that it is fully or partially disposable depending upon a particular purpose or to achieve a particular result. For example, the electrode assembly may be selectively and releasably engageable with the distal end of the shaft and/or the proximal end of shaft may be selectively and releasably engageable with the housing and the handle assembly. In either of these two instances, the forceps would be considered "partially disposable" or "reposable", i.e., a new or different electrode assembly (or electrode assembly and shaft) selectively replaces the old electrode assembly as needed.

The electrode assembly may be selectively detachable (i.e., reposable) from the shaft depending upon a particular purpose, e.g., specific forceps could be configured for different tissue types or thicknesses. Moreover, a reusable forceps could be sold as a kit having different electrodes assemblies for different tissue types. The surgeon simply selects the appropriate electrode assembly for a particular tissue type.

The forceps may also include a mechanical or electrical lockout mechanism which prevents the sealing surfaces and/or the cutting element from being unintentionally activated when the jaw members are disposed in the open configuration.

Although the subject forceps and electrode assemblies have been described with respect to preferred embodiments, it will be readily apparent to those having ordinary skill in the art to which it appertains that changes and modifications may be made thereto without departing from the spirit or scope of the subject devices. For example, although the specification and drawing disclose that the electrically conductive surfaces may be employed to initially seal tissue prior to electrically cutting tissue in one of the many ways described herein, the electrically conductive surfaces may be configured and electrically designed to perform any known bipolar or monopolar function such as electrocautery, hemostasis, and/or desiccation utilizing one or both jaw members to treat the tissue. Moreover, the jaw members in their presently described and illustrated formation may be energized to simply cut tissue without initially sealing tissue which may prove beneficial during particular surgical procedures. Moreover, the various geometries of the jaw members, cutting elements, insulators and semi-conductive materials and the various electrical configurations associated therewith may be utilized for other surgical instrumentation depending upon a particular purpose, e.g., cutting instruments, coagulation instruments, electrosurgical scissors, etc.

Various arrangements may be utilized in order to assist in the cutting of tissue. One such arrangement involves placing the tissue under a tensile force, which thereby eases the tissue separation. Tension, as defined herein, includes but is not limited to motion, force, pressure, stress and/or strain that is initiated by externally applied energy and/or internally generated energy. This tension assisted tissue division may be accomplished in a number of ways including but not limited to grasping features, expanding jaw features, shearing features, compressible features, expanding electrodes, pinch effect, moving members, moving instruments, internal or external stress or strain. Some of the possible energy types include, but are not limited to mechanical, ultrasonic, harmonic, thermal, laser and microwave. Some envisioned embodiments are discussed hereinbelow with reference to FIGS. 8A-F.

Figure 8A:
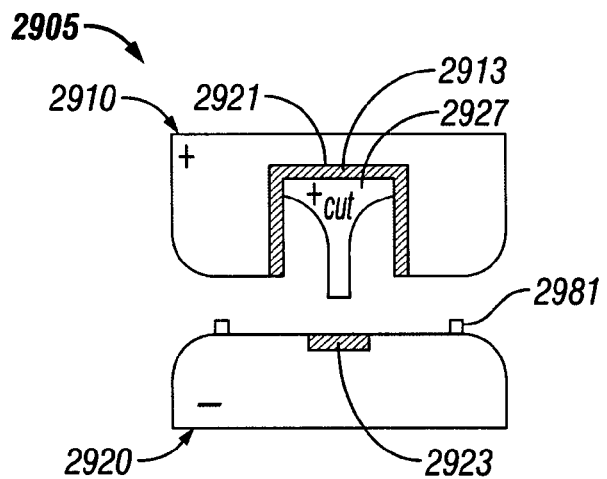
FIGS. 8A-8D are enlarged, schematic end views showing alternate configurations of the electrode assembly according to the present disclosure.

FIG. 8A shows yet another embodiment of jaw members 2910 and 2920 having an alternative electrode assembly 2905 for sealing and cutting tissue. More particularly, the electrode assembly 2905 is similar to the electrode configuration of the embodiment described with respect to FIG. 6D with the exception that graspers 2981 are provided which assist in the cutting of tissue by creating tension on the tissue. The graspers 2981 hold the tissue and provide added stress in the cut zone to assist in tissue division. The graspers 2981 may be constructed of any number of materials including ceramic, polymeric, etc. As the tissue is heated it contracts or shrinks creating tension between the graspers 2981, which, in turn, stretches the tissue and allows for cleaner separation of tissue. It is envisioned that the graspers 2981 could be used in conjunction with any of the embodiments described herein.

Figure 8B:
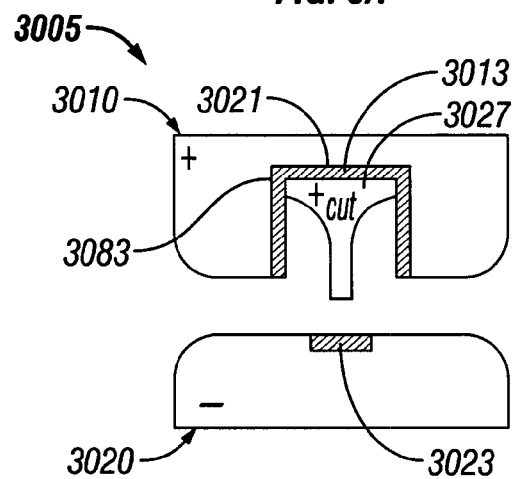

FIG. 8B shows another embodiment of jaw members 3010 and 3020 having an alternative electrode assembly 3005 for sealing and cutting tissue. More particularly, the electrode assembly 3005 is similar to that shown in FIG. 8A however, an expandable cutting electrode 3083 or jaw feature is included in order to provide additional tension to the tissue. It is envisioned for expandable cutting electrode 3083 to be constructed of a shape memory alloy (SMA) such as Nitinol. A Shape-Memory Alloy is a metal that, after being strained, at a certain temperature reverts back to its original shape. Different types of expandable and compressible materials may be used to produce tension on the tissue (e.g. silicon with a shore A durometer).

Figure 8C:
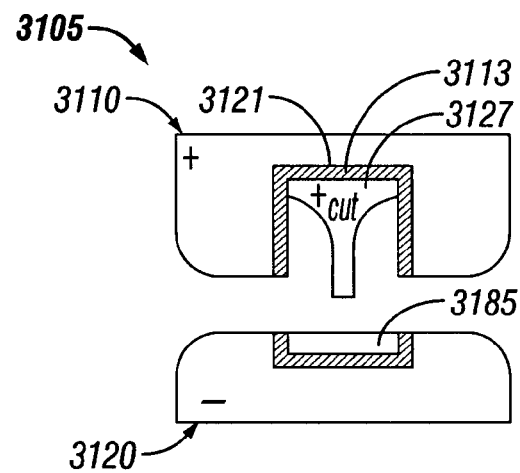

FIG. 8C shows another embodiment wherein the jaw members 3110 and 3120 have an alternative electrode assembly 3105 for sealing and cutting tissue. More particularly, the electrode assembly 3105 is similar to that shown in FIG. 8A, however, a slot 3185 defined in jaw member 3120 is further included which may work with graspers (not shown) or the expandable material 3083 mentioned above to create a tensile force upon the tissue during grasping. This design utilizes a mechanical shearing effect to create tension upon the tissue.

Figure 8D:
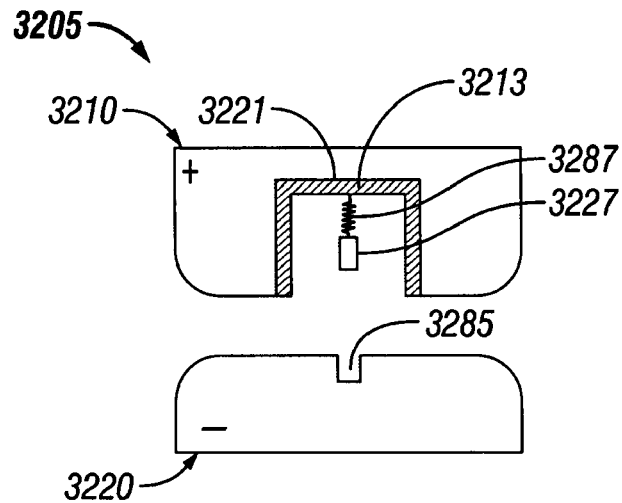

FIG. 8D shows yet another embodiment of jaw members 3210 and 3220 having an alternative electrode assembly 3205 for sealing and cutting tissue. More particularly, the electrode assembly 3205 is similar to that shown in FIG. 8A, however a spring or spring-like device 3287 is connected to the cut electrode 3227 and a slot 3285 is included to create tissue tension when grasped. Although slot 3285 is shown without an insulator an insulator could be included adjacent slot 3285. Spring 3287 may be constructed of an expandable material such as Nitinol or other known shape-memory alloys. The use of graspers 2981, expandable materials 3083 and other methods of moving the cut electrode 3227 within the cutting area are also envisioned. As mentioned hereinbefore, cut electrode 3227 may take on a variety of suitable geometrical configurations including, but not limited to, square, triangular, rounded, spiral, etc.

Figure 8E:
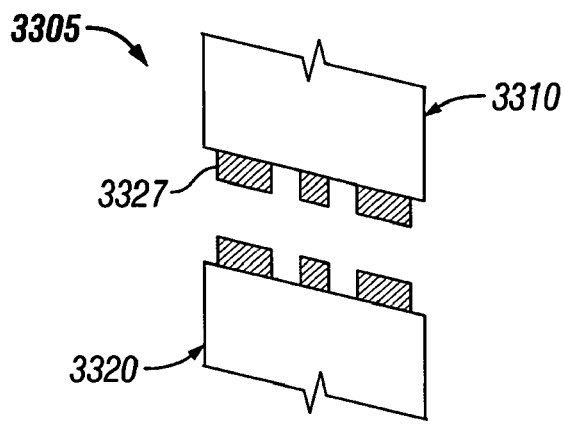
FIGS. 8E-8F are enlarged, schematic end views showing alternate configurations of the electrode assembly according to the present disclosure.
Figure 8F:
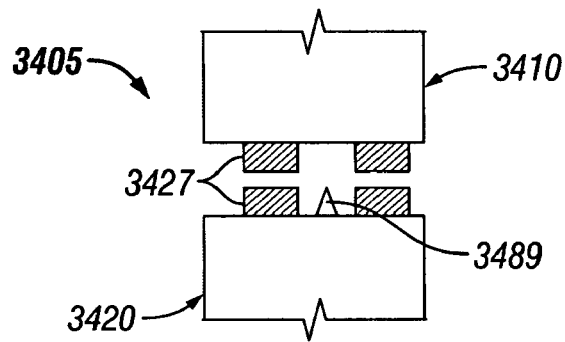

FIGS. 8E and 8F show alternate embodiments of jaw members 3310 and 3320 having an alternative electrode assembly 3305 for sealing and cutting tissue. In FIG. 8E the tissue is subjected to tension upon jaw closure. More specifically, the jaw members 3310, 3320 and electrodes 3327 are placed in an angular relationship with each other providing a tensioning effect when the jaw members 3310, 3320 are closed. Different sizes and shapes for the electrodes 3327 are contemplated. The numerous geometries and configurations of electrodes 3327 and jaw members 3310, 3320 described herein may be utilized in accordance with this embodiment.

FIG. 8F shows jaw member 3420 having a tissue tensioning mechanism 3489 disposed between electrodes 3427. As tissue shrinkage occurs the tissue comes into contact with the tensioning mechanism 3489, further stretching the tissue and providing additional tension. As shown in FIG. 8F, the tensioning mechanism 3489 may have a pointed or triangular tip which aides in tissue division. However, multiple geometrical configurations are possible. The tensioning mechanism 3489 could be rounded, rectangular, square, spiral, frusto-conical, etc. In FIG. 8F the tensioning mechanism 3489 is shown on the lower jaw 3420, however, the mechanism may also be on the upper jaw 3410, lower jaw 3420, or both. Moreover, tensioning mechanisms 3489 may be placed in different and varying locations on jaws 3410, 3420.

Figure 9A:
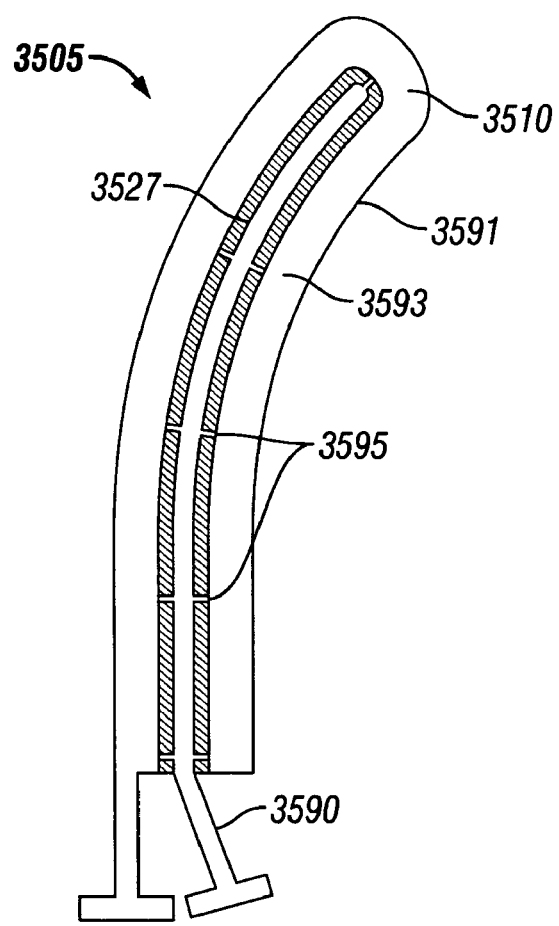
FIGS. 9A-9B are enlarged views showing alternate configurations of electrodes having a curved jaw.
Figure 9B:
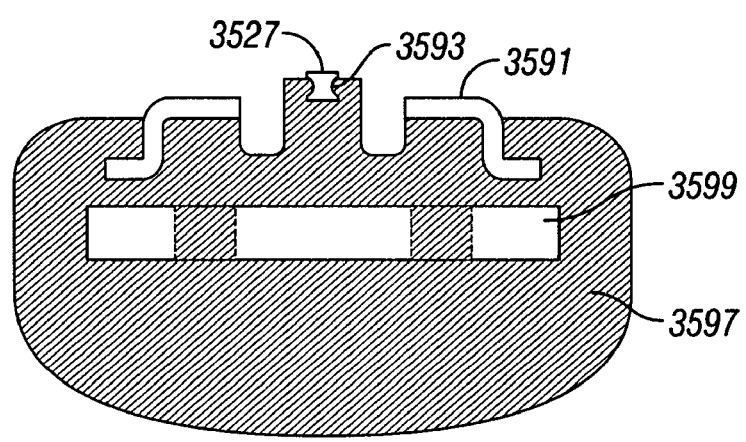

The electrode assembly 3505 as shown in FIG. 9A may be formed in a variety of suitable ways. FIGS. 9A and 9B show electrodes formed by using metal deposition/photochemical etching or stamping processes. Although, only one jaw member 3510 is shown in the figures, the opposing jaw member 3520 is envisioned to have a similar or complimentary configuration. FIG. 9A shows a seal plate 3591 having an electrically conductive tissue sealing surface 3593 and a cut electrode or electrically conductive cutting element 3527. The seal plate 3591 may be photochemically etched or stamped and then formed into its final shape by stages in a progressive stamping die. The stamping die would raise the cut electrode 3527 above the seal surface 3593. Multiple thin supports 3595 may be utilized to hold the cut electrode 3527 in place, only to be subsequently lanced out after the molding step to ensure electrical insulation. Seal plate 3591 may be backed by a rigid structural support 3599 that may be perforated to allow overmolded material to flow therethrough. Seal plate 3591 may then be overmolded or bonded to the final jaw shape. Crimping terminals 3590 may be included to hold the wires or electrical connections in electrical communication with the seal plates 3591. The electrical connections may also be soldered or welded.

FIG. 9B shows a cross-sectional view of the seal plate 3591 of FIG. 9A. Raised cut electrode 3527 is shown having an indentation 3593 from chemical milling or other methods. This indentation 3593 is located on the side of cut electrode 3527 and serves to hold electrode 3527 in place once embedded in plastic or other insulating materials. Structural backing 3599 (which may be perforated to allow overmolded material to flow therethrough) is shown underneath seal plate 3591. Seal plate 3591 is shown surrounded by an insulative overmolded structure 3597.

Figure 10A:
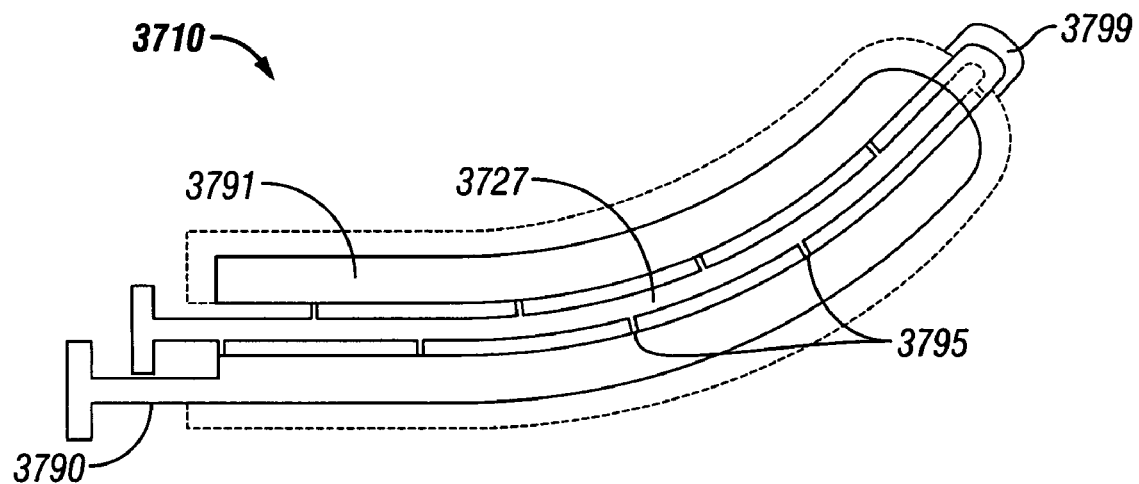
FIGS. 10A-10D are enlarged views showing alternate configurations of electrodes having a curved jaw.

FIG. 10A shows an alternate embodiment of the seal plate 3791 of the present disclosure. In this embodiment a curved jaw shape is shown having a current path 3799 or bridge located at the distal end of the seal plate 3791. As shown above the seal plate 3791 may extend beyond the supporting jaw member 3710 and the cut electrode 3727 may extend through the center of the jaw member 3710. The outer edges of the curved jaw 3710 may be used for manipulating and sealing tissue.

Figure 10B:
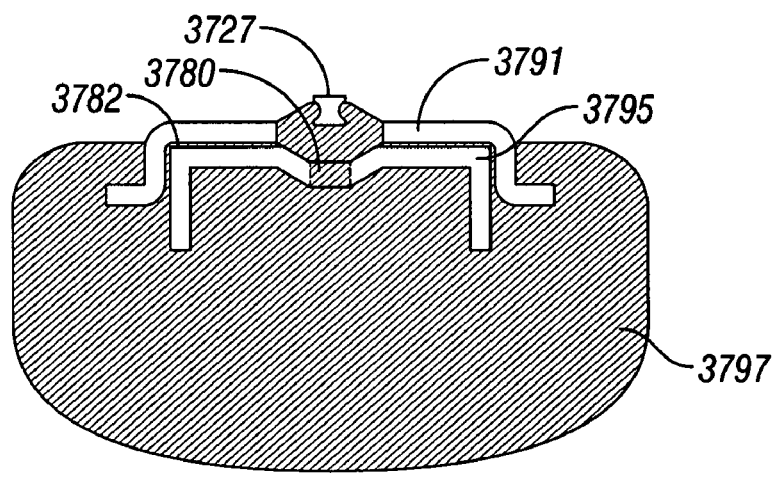

FIG. 10B is similar to that shown in FIG. 9B showing a cross-sectional view of the seal plate 3791 of FIG. 10A. FIG. 10B shows a flow channel 3780 with perforations located beneath the cut electrode 3727. An optional insulation layer 3782 may be provided between seal plate 3791 and rigid structural support or backing 3795. Rigid structural support 3795 may contain perforations that allow insulative overmolded structure 3797 to flow therethrough during the manufacturing process. This provides additional support for the seal plate 3791. As mentioned hereinbefore, the electrically conductive tissue sealing surfaces may be formed using a variety of suitable techniques including, but not limited to, photochemical etching and stamping processes.

Figure 10C:
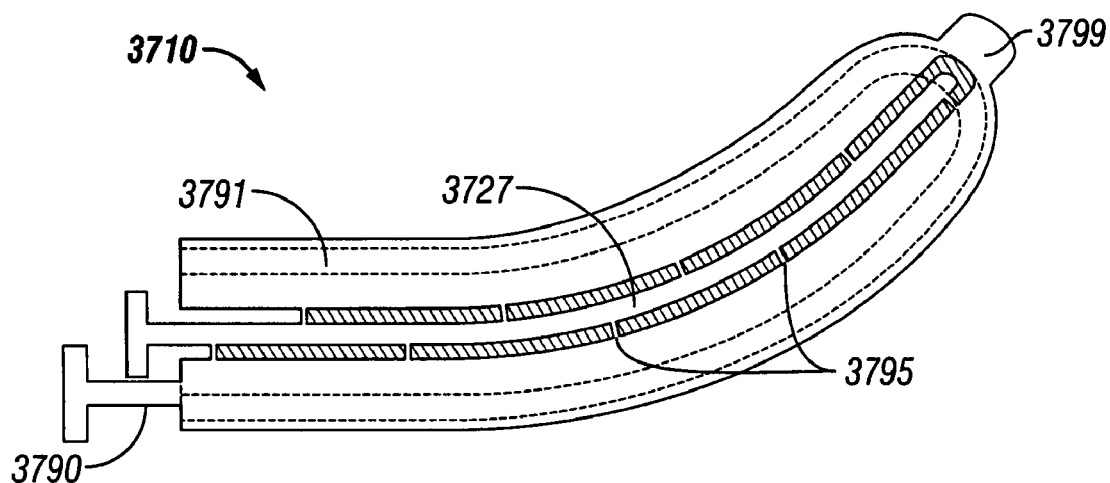
Figure 10D:
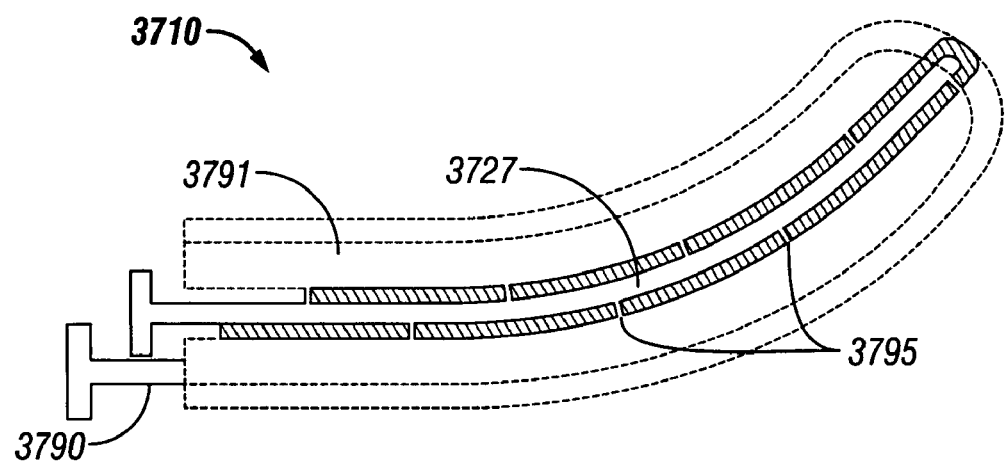

FIG. 10C shows jaw member 3710 according to another embodiment of the present disclosure having bridge 3799. Bridge 3799 may protrude outward from jaw 3710 to provide additional functions such as mechanical dissection. Alternatively, bridge 3799 could be folded under and covered by overmolded structure 3797. FIG. 10D shows jaw member 3710 in its final bent shape.

Figure 11A:
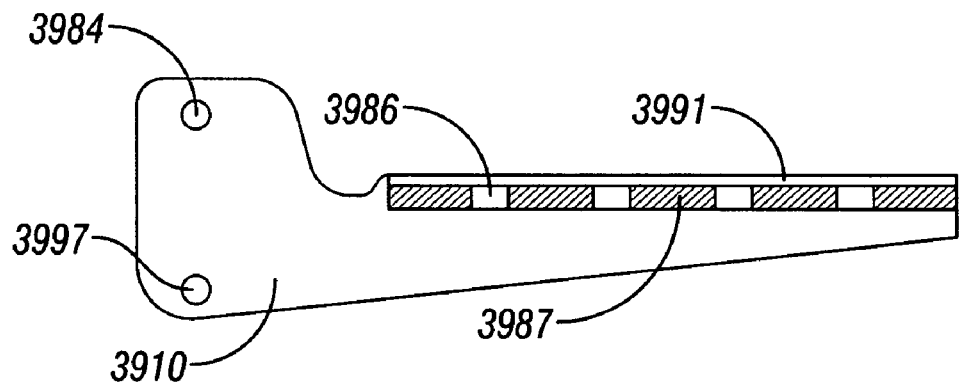
FIGS. 11A-11C are enlarged views showing alternate configurations of electrodes of the present disclosure.

FIG. 11A shows jaw member 3910 according to yet another embodiment of the present disclosure. Jaw member 3910 includes pivot point 3984 located on the proximal end of jaw member 3910. Jaw member 3910 is configured to pivot about the pivot point 3984 and may be affixed with a pin, bolt, screw, or alternative mechanism. Hole 3997 can be used to open/close or otherwise move the jaw member. Jaw member 3910 may further include flow holes 3986 and seal plate 3991. An insulator 3987 similar to 3782 may be used and constructed of a number of different materials including, but not limited to, polymeric, ceramic or other materials.

Figure 11B:
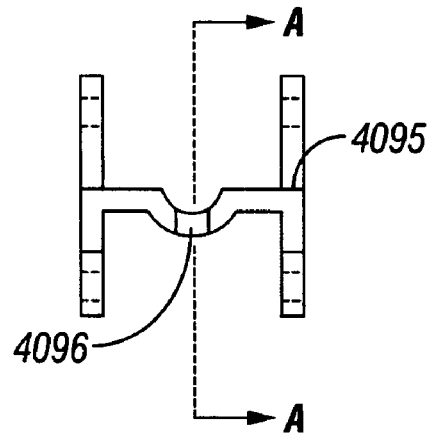

FIG. 11B shows an example of structural backing 4095 which may be used to support the jaw members. Structural backing 4095 may be perforated to allow the overmolded material to flow therethrough during manufacturing for securing purposes. The backing 4095 may be straight or curved, depending upon the shape of the jaw member. The backing 4095 may also be formed by stamping, photo-etching, machining, etc.

Figure 11C:
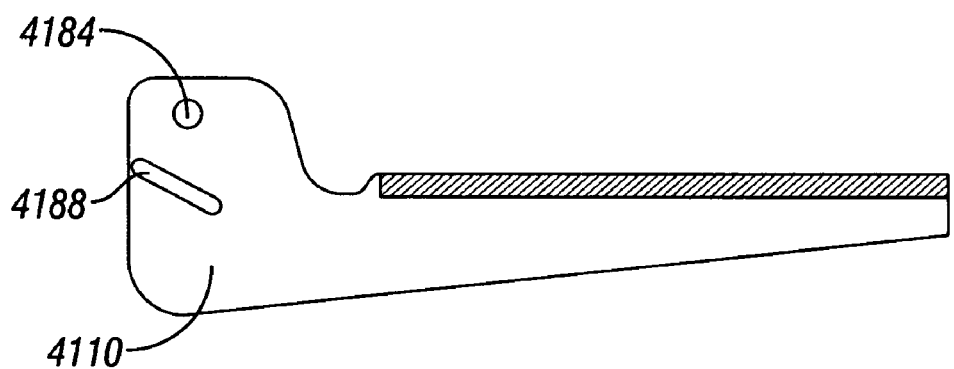

FIG. 11C shows yet another embodiment of a jaw member 4110 according to the present disclosure without the flow holes 3986 shown in FIG. 11A. However, in this embodiment jaw member 4110 further includes a cam slot 4188 defined therein in addition to the pivot hole 4184 of FIG. 11A. Cam slot 4188 is configured and dimensioned to regulate the movement of jaw member 4110 from the open to close positions.

The present disclosure further relates to devices and methods for modulating or altering the conductivity of tissue during sealing, coagulation and/or cutting of tissue. As used herein "conductivity" refers to a measure of the ability of a tissue, solution, or combination thereof to carry an electrical current. Accordingly the term relates to the ability for energy to flow through tissue, which is directly dependent on the tissue's hydration level. Tissue which is well hydrated generally tends to have low impedance. Accordingly, well hydrated tissue has a low opposition or resistance to the flow of electrical current. Thus, tissue that is dehydrated or poorly hydrated has a high impedance and tends to oppose or resist the flow of electrical current therethrough. The devices and methods in accordance with the present disclosure can improve tissue conductivity and/or lower tissue impedance by irrigating the tissue to be affected by electrosurgery with one or more fluids. It is also envisioned that the devices and methods in accordance with the present disclosure can also raise tissue impedance by removing fluids surrounding and/or within the tissue to be affected by the electrosurgical procedure.

It is envisioned that the fluid material can be applied to tissue during any electrical surgical procedure, including but not limited to sealing, coagulation and/or cutting of tissue in surgical applications. The fluid can be non-conductive fluid, conductive fluid, or combinations thereof. Suitable non-limiting examples of non-conductive fluids include aqueous solutions, 1.5% glycine, 3% sorbitol, 5% mannitol, sterile water, and combinations thereof. Suitable non-limiting examples of conductive fluid materials include aqueous solutions, saline solutions such as 0.9% saline solution, salt solution, electrolyte containing solution, and combinations thereof. Suitable saline solution may refer to a conductive, electrolyte containing, low viscosity fluid including sodium chloride (NaCl) and distilled water. As used herein "conductive" relates to a measure of the solutions ability to carry electricity.

Figure 12A:
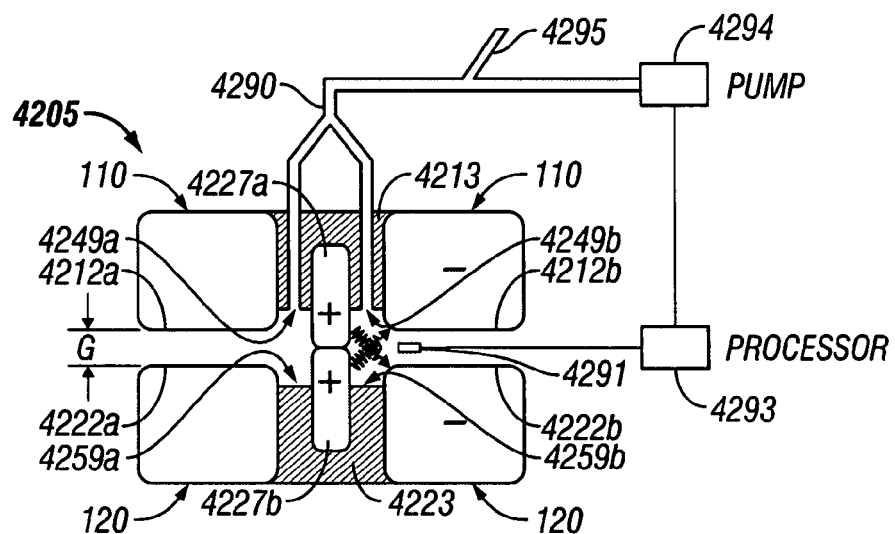
FIGS. 12A-12F are enlarged, schematic end views showing a variety of different electrode assemblies according to the present disclosure with various channels.

Referring now to FIGS. 12A-12F, various enlarged, schematic end views showing a variety of different electrode assemblies according to the present disclosure with channels for irrigating tissue before, during and/or after electrical cutting are shown. With respect to FIG. 12A, the conductive cutting elements 4227a and 4227b are oriented in opposing, vertical registration within respective insulators 4213 and 4223 of jaw members 110 and 120. Cutting elements 4227a and 4227b may be substantially dull so as to not inhibit the sealing process (e.g., premature cutting) during the sealing phase of the electrosurgical activation. In other words, the surgeon is free to manipulate, grasp and clamp the tissue for sealing purposes without the cutting elements 4227a and 4227b mechanically cutting into the tissue. Moreover, in this instance, tissue cuffing can only be achieved through either: 1) a combination of mechanically clamping the tissue between the cutting elements 4227a and 4227b and applying electrosurgical energy from the cutting elements 4227a and 4227b, through the tissue and to the return electrodes, i.e., the electrically conductive tissue contacting surfaces 4212b and 4222b as shown in FIG. 12A; or 2) applying electrosurgical energy from the cutting elements 4227a and 4227b through the tissue and to the return tissue contacting surfaces 4212b and 4222b.

The geometrical configuration of the cutting elements 4227a and 4227b may play an important role in determining the overall effectiveness of the tissue cut. For example, the power density and/or current concentration around the cutting elements 4227a and 4227b is based upon the particular geometrical configuration of the cutting elements 4227a and 4227b and the cutting elements' 4227a and 4227b proximity to the return electrodes, i.e., tissue contacting surfaces 4212b and 4222b. Certain geometries of the cutting elements 4227a and 4227b may create higher areas of power density than other geometries. Moreover, the spacing of the return electrodes 4212b and 4222b to these current concentrations affects the electrical fields through the tissue. Therefore, by configuring the cutting elements 4227a and 4227b and the respective insulators 4213 and 4223 within close proximity to one another, the electrical power density remains high, which is ideal for cutting tissue and the instrument will not short due to accidental contact between conductive surfaces. The relative size of the cutting elements 4227a and 4227b and/or the size of the insulator 4213 and 4223 may be selectively altered depending upon a particular or desired purpose to produce a particular surgical effect.

In addition, fluid may be administered by the surgeon to modulate or alter the electrical fields through the tissue. Fluid may be administered independently or automatically activated by a sensor 4291 connected to a processor 4293 suitable for activating a pump 4294 in communication with channel 4290. The fluid may be added before, during, and/or after cutting, sealing or other electrosurgical application in order to modulate the electrical fields through the tissue. One or more fluids may be employed through a channel 4290 which passes through insulator 4213 to assure that the tissue is properly hydrated. An audible or visual indicator (not shown) may be employed to assure the surgeon that the tissue is hydrated and/or the surgeon may be required to activate a pump, or port 4295 to irrigate the site. For example, a smart sensor 4291 or feedback algorithm may be employed to determine tissue conductivity prior to cutting. The smart sensor or feedback loop may also be configured to automatically switch electrosurgical energy to the cutting element 4227a (and/or 4227b) once the smart sensor determines that the tissue is properly hydrated. The electrical configuration of the electrically conductive sealing surfaces 4212a, 4212b and 4222a, 4222b may also be automatically or manually altered during the sealing and cutting processes to effect accurate and consistent tissue sealing and cutting.

It is also envisioned that the device may use a closed loop control that would sense measured outputs levels such as, impedance, currant, voltage, or power during RF activation and inject the appropriate amount of hydration to maintain a specific level or control the rise or decay of a specific output. For example, sensor 4291 could be connected to a pump system that increases flow and delivers hydration based on impedance levels by either maintaining a specific value or controlling the rate of rise or decay.

Turning now to the particular embodiments of the electrode assembly 4205, as disclosed herein, which show the various polarities during the tissue cutting phase, FIG. 12A as mentioned above includes first and second jaw members 110 and 120 having an electrode assembly 4205 disposed thereon. More particularly, the electrode assembly 4205 includes first electrically conductive sealing surfaces 4212a and 4212b each disposed in opposing registration with second electrically conductive sealing surfaces 4222a and 4222b on jaw members 110 and 120, respectively. Insulator 4213 electrically isolates sealing surfaces 4212a and 4212b from one another allowing selective independent activation of the sealing surfaces 4212a and 4212b. Insulator 4223 separates sealing surfaces 4222a and 4222b from one another in a similar manner thereby allowing selective activation of sealing surfaces 4222a and 4222b.

Each insulator 4213 and 4223 is set back a predetermined distance between the sealing surfaces 4212a, 4212b and 4222a, 4222b to define a recess 4249a, 4249b and 4259a, 4259b, respectively, which, as mentioned above, affects the overall power densities between the electrically activated surfaces during both the sealing and cutting phases. Cutting element 4227a is disposed within and/or deposited on insulator 4213 and extends inwardly therefrom to extend beyond the sealing surfaces 4212a, 4212b by a predetermined distance. In the embodiments wherein only one cutting element, e.g., 4227a, is shown, the cutting element 4227a extends beyond the sealing surfaces 4212a, 4212b and 4222a and 4222b to define the aforementioned gap range between the opposing sealing surfaces 4212a, 4222a and 4212b and 4222b. When two (or more) cutting elements 4227a and 4227b are employed (e.g., at least one disposed within each insulator 4213 and 4223) the combination of the cutting elements 4227a and 4227b yield the desired gap distance within the working gap range.

During sealing, the opposing sealing surfaces 4212a, 4222a and 4212b, 4222b are activated to seal the tissue disposed therebetween to create two tissue seals on either side of the insulators 4213 and 4223. During the cutting phase, the cutting elements 4227a and 4227b are energized with a first electrical potential "+" and the right opposing sealing surfaces 4212b and 4222b are energized with a second electrical potential "−". This creates a concentrated electrical path between the potentials "+" and "−" through the tissue to cut the tissue between the previously formed tissue seals. Once the tissue is cut, the jaw members 110 and 120 are opened to release the two tissue halves.

Figure 12B:
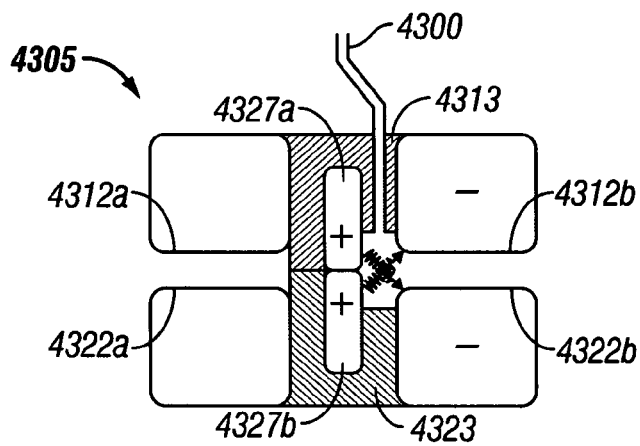

FIG. 12B discloses another embodiment according to the present disclosure that includes similar elements as described above with respect to FIG. 12A, namely, sealing surfaces 4312a, 4312b and 4322a, 4322b, insulators 4313 and 4323 and cutting elements 4327a and 4327b with the exception that the left side of each insulator 4313 and 4323 is extended beyond sealing surfaces 4312a and 4322a to a position that is flush with the cutting elements 4327a and 4327b. The right side of each insulator 4313 and 4323 is set back from sealing surfaces 4312b and 4322b, respectively. Configuring the electrode assembly 4305 in this fashion may reduce stray current concentrations between electrically conductive surfaces 4312a, 4312b and 4322a, 4322b and cutting elements 4327a and 4327b especially during the cutting phase. In addition, channel 4300 is shown passing through insulator 4313. Configuring the electrode assembly 4305 in this fashion provides a channel for irrigating tissue with a fluid passed through insulator 4313 and be applied to tissue immediately adjacent cutting elements 4327a and 4327b before, during and/or after the cutting phase.

Figure 12C:
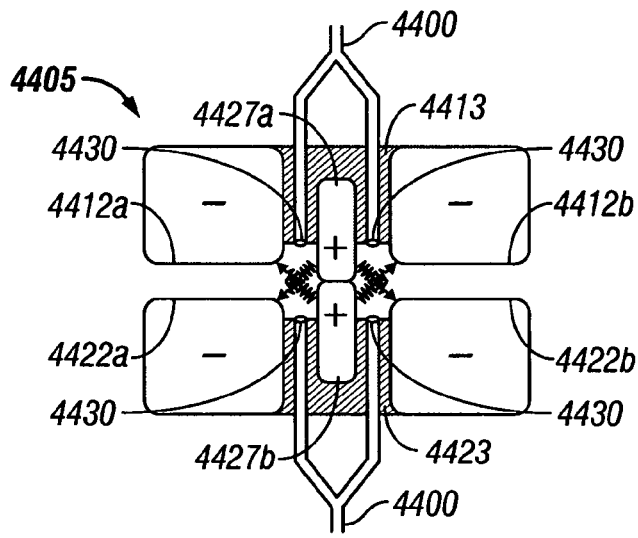

FIG. 12C discloses yet another embodiment according to the present disclosure and includes similar elements as above, namely, sealing surfaces 4412a, 4412b and 4422a, 4422b, insulators 4413 and 4423 and cutting elements 4327a and 4327b. With this particular embodiment, during the cutting phase, both sets of opposing sealing surfaces 4412a, 4422a and 4412b, 4422b are energized with the second electrical potential "−" and the cutting elements 4427a and 4427b are energized to the first electrical potential "+". It is believed that this electrode assembly 4405 may create concentrated electrical paths between the potentials "+" and "−" through the tissue to cut the tissue between the previously formed tissue seals. In addition, channel 4400 is shown passing through insulator 4413 and 4423. Portions of channel 4400 branch around cutting elements 4427a and 4427b. Channel 4400 ends at orifice 4430 adjacent to cutting elements 4427a and 4427b. Configuring the electrode assembly 4405 in this fashion provides a channel 4500 for irrigating tissue with a fluid immediately adjacent cutting elements 4427a and 4427b before, during and/or after the cutting phase.

Figure 12D:
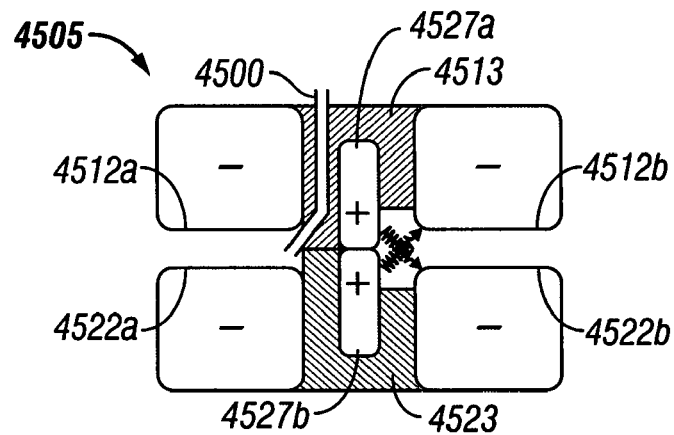

FIG. 12D shows an electrode assembly 4505 configuration similar to FIG. 12B with a similar electrical configuration to the embodiment of FIG. 12C. The electrode assembly 4505 includes similar components as described above, namely, sealing surfaces 4512a, 4512b and 4522a, 4522b, insulators 4513 and 4523 and cutting elements 4527a and 4527b. The opposing sealing electrodes 4512a, 4522b and 4512a, 4522b are energized to the second electrical potential "−" during the cutting phase, which as described above is believed to enhance tissue cutting. With particular embodiments like FIGS. 12C and 12D, it may be easier to manufacture the electrode assembly 4505 such that all of the sealing surfaces 4512a, 4512b and 4522a, 4522b are energized to the same electrical potential rather than employ complicated switching algorithms and/or circuitry to energize only select sealing surfaces like embodiments in FIGS. 12A and 12B. In addition, channel 4500 is shown passing through insulator 4513. Configuring the electrode assembly 4505 in this fashion provides a channel for irrigating tissue adjacent cutting elements 4527a and 4527b before, during and/or after the cutting phase.

Figure 12E:
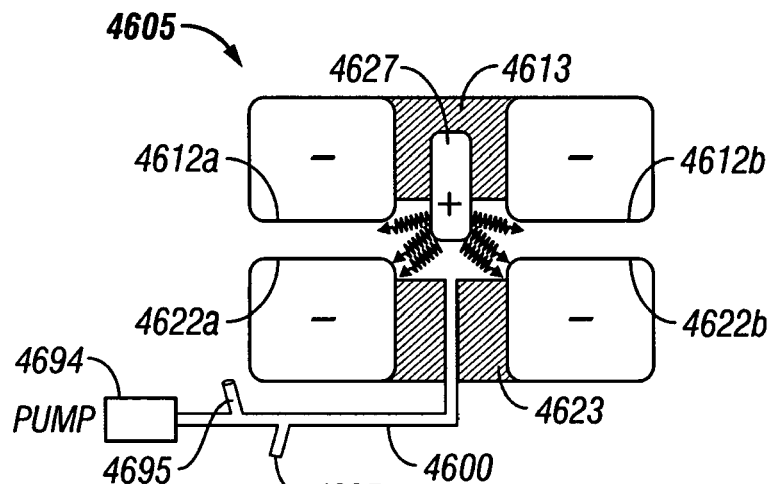

FIG. 12E shows yet another embodiment of the electrode assembly 4605 that includes opposing sealing surfaces 4612a, 4622a and 4612b, 4622b, cutting element 4627 and insulators 4613 and 4623. In this particular embodiment, the electrode assembly 4605 only includes one cutting element 4627 disposed within insulator 4613 for cutting tissue. The cutting element 4627 is disposed opposite insulator 4623, which provides a dual function during activation of the electrode assembly 4605: 1) provides a uniform gap between sealing surfaces 4612a, 4622a and 4612b, 4622b during the sealing phase; and 2) prevents the electrode assembly 4605 from shorting during the sealing and cutting phases. During activation, the cutting element 4627 is energized to a first potential "+" and the opposing sealing surfaces 4612a, 4622a and 4612b, 4622b are energized to a second electrical potential "−" which creates an area of high power density between the two previously formed tissue seals and cuts the tissue. In addition, channel 4600 is shown passing through insulator 4623. Configuring the electrode assembly 4605 in this fashion provides a channel for irrigating tissue adjacent cutting elements 4627a and 4627b before, during and/or after the cutting phase. Channel 4600 is also shown schematically attached to a pump 4694. At least two ports 4695 are shown for adding and/or removing fluid from device 4605. Configuring the electrode assembly 4605 in this fashion provides a surgeon with the option of using a pump, or manual methods to move the fluid through the device.

Figure 12F:
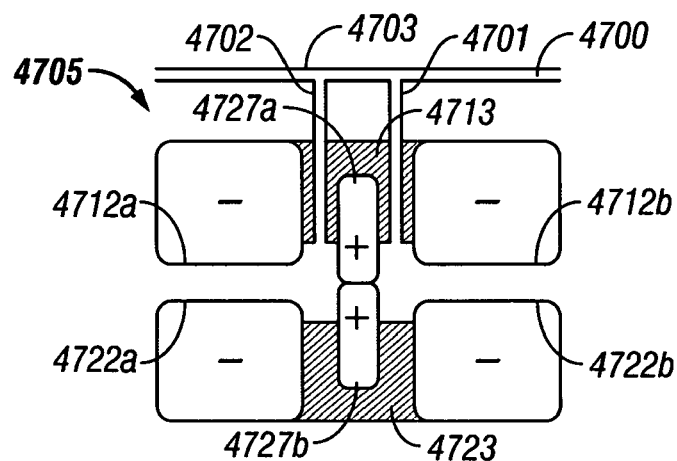

FIG. 12F shows yet another alternate embodiment of the electrode assembly 4705 that includes similar elements as described above, namely, sealing surfaces 4712a, 4712b and 4722a, 4722b, cutting elements 4727a and 4727b and insulators 4713 and 4723. During activation, only three of the four sealing surfaces are energized to the second potential "−", e.g., sealing surfaces 4712a, 4712b and 4722b while the cutting elements 4727a and 4727b are energized to the first potential "+". In addition, channel 4700 is shown with branch 4701 and branch 4702 extending away from central line 4703. Branches 4701 and 4702 pass through insulator 4713. Configuring the electrode assembly 4705 in this fashion provides a channel configuration for irrigating tissue with a fluid adjacent cutting elements 4727a and 4727b before, during and/or after the cutting phase.

Figure 13:
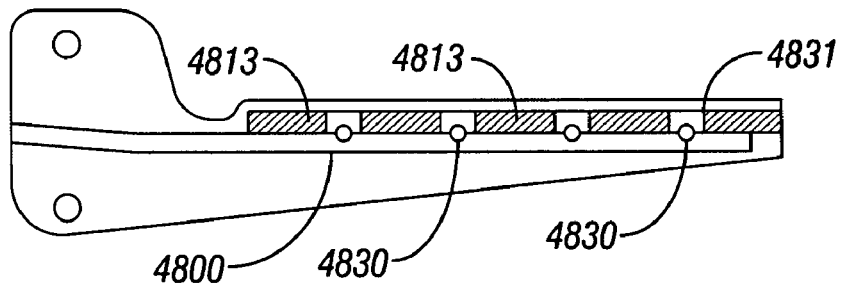
FIG. 13 is an enlarged view showing alternate configurations of electrodes of the present disclosure.

FIG. 13 shows yet another embodiment of a jaw member 4810 according to the present disclosure with the one or more channels similar to those shown in FIG. 12A-12F. It is envisioned that the channel 4800 extends longitudinally down jaw member 4810. Various apertures 4830 can be placed along the channel to allow fluid passing therein to enter or exit the channel. By placing the apertures below pre-selected holes 4831 or openings in the insulative layer 4813, fluid can pass through insulator 4813 and be applied to tissue adjacent cutting elements (not shown in FIG. 13) before, during and/or after the cutting phase. It is envisioned that the insulator layer 4813 can be porous or sponge like so that fluid can pass there through.

Figure 14:
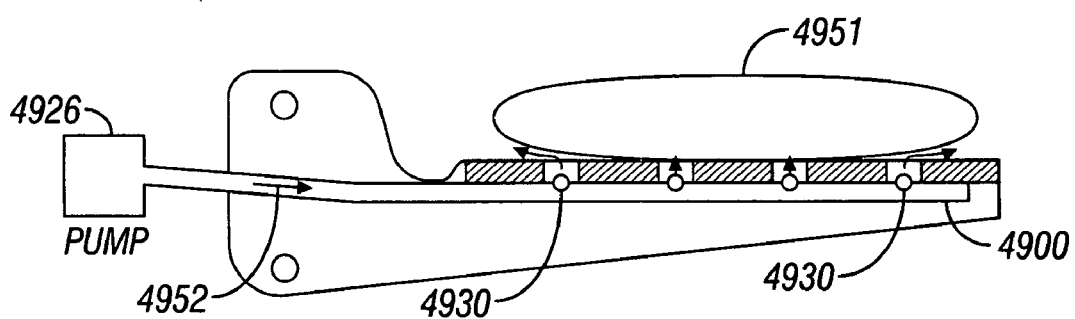
FIG. 14 is an enlarged view showing alternate configurations of electrodes of the present disclosure.

FIG. 14 shows yet another embodiment of a jaw member 4910 according to the present disclosure with the one or more channels similar to those shown in FIG. 12A-12F and 13. It is envisioned that the channel 4900 extends longitudinally down jaw member 4910. Various apertures 4930 can be placed along the channel to allow fluid passing therein to enter or exit the channel. By placing a pump 4926 along the length of channel 4900 in fluid communication therewith, fluid can be pushed through the channel in the direction of arrow 4952 and contact tissue 4951. Any manual or automatic pump 4926 can be positioned upstream from the apertures 4930. The pump 4926 can be any pump suitable for moving fluid to and from the tissue before, during and/or after a procedure such as sealing, coagulation, and/or cutting of tissue. It is envisioned that the pump can be reversed to move fluid away from tissue 4951 opposite the direction of arrow 4952.

Figure 15:
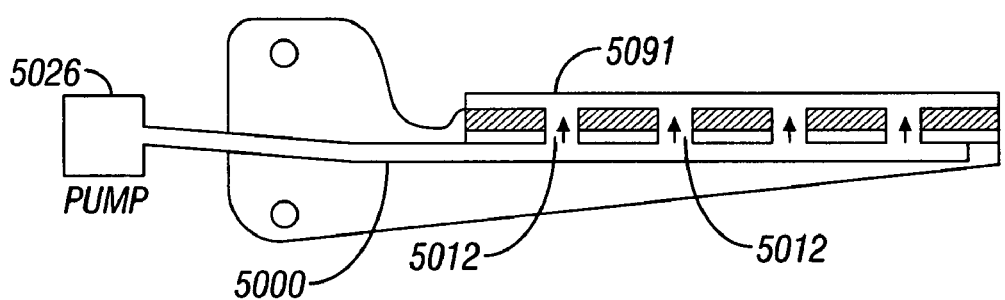
FIG. 15 is an enlarged view showing alternate configurations of electrodes of the present disclosure.

FIG. 15 shows yet another embodiment of a jaw member 5010 according to the present disclosure with the one or more channels similar to those shown in FIG. 12A-12F, FIG. 13 and FIG. 14. It is envisioned that the channel 5000 extends longitudinally down jaw member 5010 and branches in to a plurality of irrigation ports 5012 which pass through the insulative layer, and terminate adjacent to the surface of the seal plate 5091.

Figure 16:
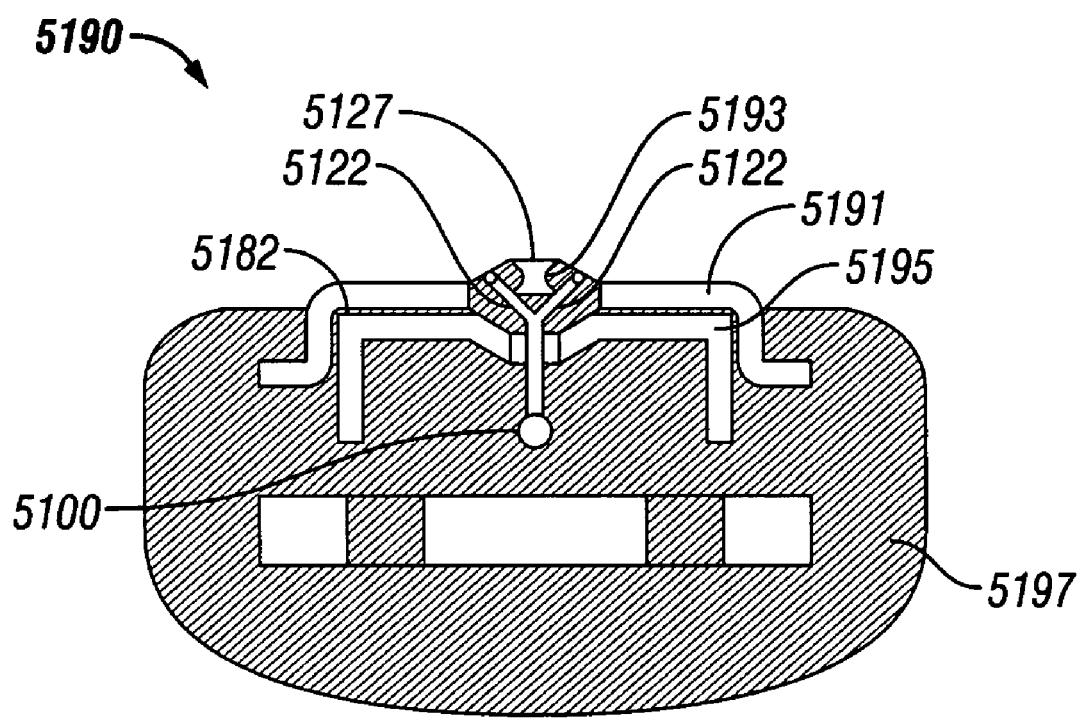
FIG. 16 are enlarged cross-sectional view showing alternate configurations of electrodes having channels.

FIG. 16 shows a cross-sectional view of the seal plate 5190 in an embodiment according to the present disclosure. Raised cut electrode 5127 is shown having an indentation 5193 from chemical milling or other methods. This indentation 5193 is located on the side of cut electrode 5127 and serves to hold electrode 5127 in place once embedded in plastic or other insulating materials. Structural backing 5195 (which may be perforated to allow overmolded material to flow therethrough) is shown underneath seal plate 5191. Seal plate 5191 is shown surrounded by an insulative overmolded structure 5197. Channel 5100 is shown with an irrigation port 5122 which extends away from the channel 5100 and branches around raised cut electrode 5127.

Figure 17:
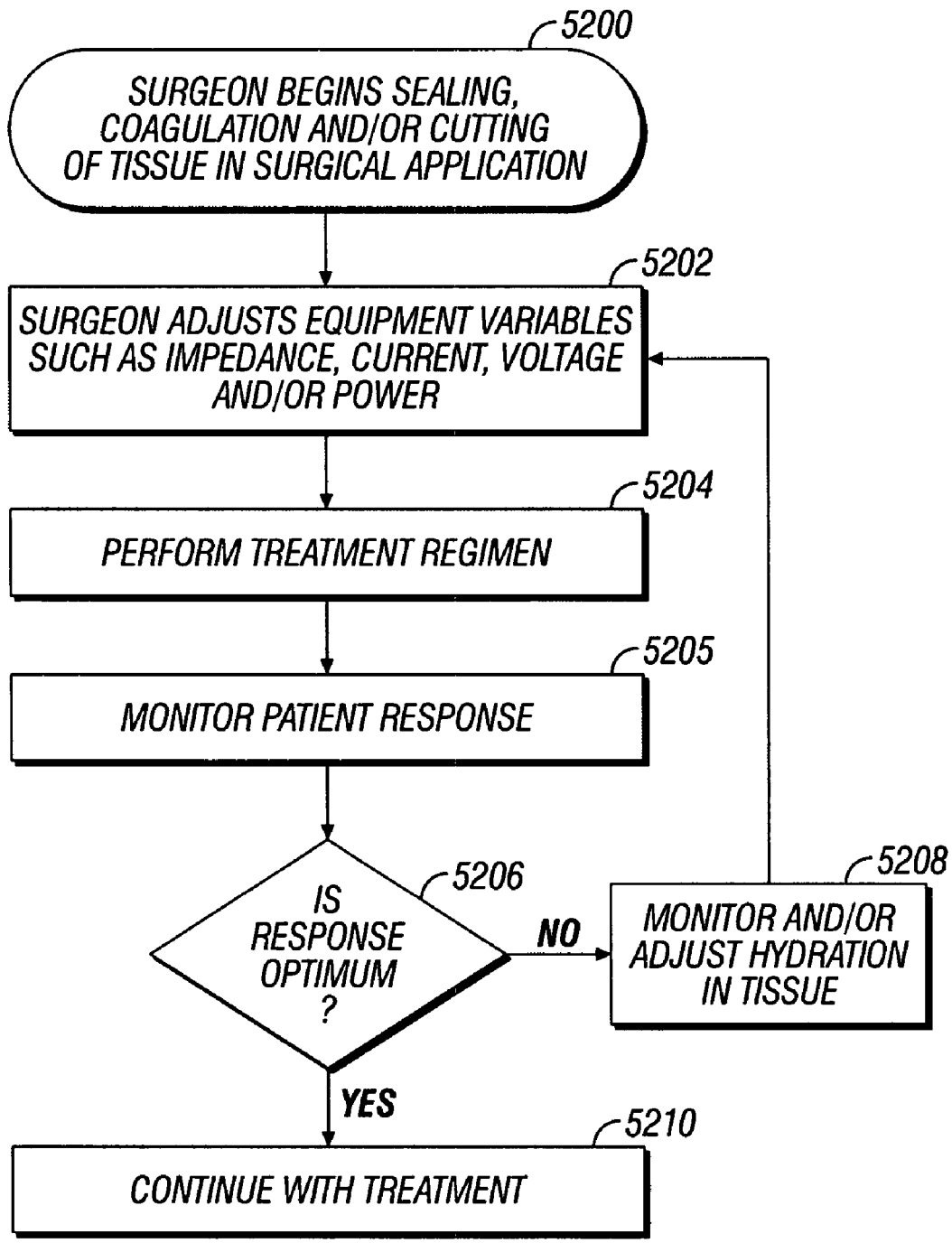
FIG. 17 is as a flowchart of the steps performed by an embodiment of an electrosurgical device with one or more channels in accordance with the present disclosure.

The flowchart of FIG. 17 illustrates possible steps performed by a surgeon in a method embodiment of the present disclosure. Beginning with step 5200, the surgeon prepares the patient for the electrosurgical application, such as by positioning the electrosurgical apparatus in the patient's body adjacent to the tissue to be affected by the procedure. The treatment parameters are set in step 5202, where the surgeon monitors various equipment variables such as impedance, current, voltage, power, and combinations thereof. In step 5204, the surgeon begins performing the treatment regimen. In step 5205, the surgeon continues to monitor variables such as impedance, current, voltage, power, and combinations thereof. The monitoring of variables and responses are further evaluated in step 5206. If the patient is responding appropriately to the treatment, then the treatment continues in step 5210 for the duration of the treatment session. However, if the patient is experiencing difficulties or other inappropriate responses are detected such as high impedance in the affected tissue, then the treatment session is stopped and the treatment parameters are adjusted in steps 5208 and 5202. In step 5208, the tissue is irrigated with a fluid. After readjusting the parameters, a new round of treatment is initiated, as previously described, continuing on from step 5202.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An end effector assembly for use with an instrument for sealing, coagulating and/or cutting vessels and/or tissue, the end effector assembly comprising:
   - a pair of opposing first and second jaw members at least one of which is movable relative to the other from a first position wherein the jaw members are disposed in spaced relation relative to one another to a second position wherein the jaw members cooperate to grasp tissue therebetween;
   - each jaw member including an electrically conductive tissue sealing surface extending along a length thereof, each tissue sealing surface adapted to connect to a source of electrosurgical energy such that the tissue sealing surfaces are capable of conducting electrosurgical energy through tissue grasped therebetween to effect a seal;
   - an insulative support element configured to support each electrically conductive tissue sealing surface;
   - a first electrically conductive cutting element disposed within the insulative support element of the first jaw member;
   - a second electrically conductive cutting element disposed within the insulative support element of the second jaw member, the second electrically conductive cutting element generally opposing the first electrically conductive cutting element; and
   - at least one channel defined within at least one of the insulative support elements, the at least one channel configured to transport fluid adjacent to the electrically conductive cutting element.

2. An end effector assembly according to claim 1, wherein the channel further comprises at least one port configured to at least deliver fluid through the port.

3. An end effector assembly of claim 2, wherein the fluid comprises at least one of a conductive fluid, a non-conductive fluid, and combinations thereof.

4. An end effector assembly of claim 3, wherein the conductive fluid comprises aqueous solutions, saline solutions, salt solutions, electrolyte containing solutions, and combinations thereof.

5. An end effector assembly of claim 3, wherein the non-conductive fluid comprises at least one of aqueous solutions, a solution having 1.5% glycine, 3% sorbitol, 5% mannitol, sterile water solution, and combinations thereof.

6. An end effector assembly according to claim 1, wherein the channel is in communication with at least one pump.

7. An end effector assembly according to claim 1, further comprising a sensor configured to monitor the conductivity of tissue disposed between the jaws.

8. An end effector assembly according to claim 1, wherein each insulative support element is configured to at least partially extend to a position which is at least substantially flush with its respective cutting element.

\* \* \* \* \*